United States Patent [19]

Matsuo et al.

[11] Patent Number: 5,583,135
[45] Date of Patent: Dec. 10, 1996

[54] HETEROTRICYCLIC DERIVATIVES, PROCESS FOR THEIR PREPARATION AND PHARMACEUTICAL COMPOSITIONS CONTAINING THEM

[75] Inventors: Masaaki Matsuo, Toyonaka; Kiyoshi Tsuji, Kishiwada; Katsuya Nakamura, Takatsuki; Glen W. Spears, Ikeda, all of Japan

[73] Assignee: Fujisawa Pharmaceutical Co., Ltd., Osaka, Japan

[21] Appl. No.: 256,621

[22] PCT Filed: Jan. 26, 1993

[86] PCT No.: PCT/JP93/00090

§ 371 Date: Jul. 26, 1994

§ 102(e) Date: Jul. 26, 1994

[87] PCT Pub. No.: WO93/15083

PCT Pub. Date: Aug. 5, 1993

[30] Foreign Application Priority Data

Jan. 27, 1992 [GB] United Kingdom ............. 9201836
Nov. 16, 1992 [GB] United Kingdom ............. 9224012

[51] Int. Cl.⁶ ............. C07D 498/06; C07D 513/04; A61K 31/535; A61K 31/54
[52] U.S. Cl. ............. 514/230.2; 514/224.2; 514/226.8; 514/228.2; 514/224.5; 544/101; 544/52; 544/54; 544/58.6; 544/14
[58] Field of Search ............. 514/224.5, 230.2; 544/101, 52

[56] References Cited

U.S. PATENT DOCUMENTS 4,547,511  10/1985  Eriksoo et al. ............. 514/312

OTHER PUBLICATIONS

Klippel, J. H. et al. *Internal Medicine*, Stein, J. H. et al. ed. (Mosby, St. Louis), pp. 2422–2423 (1994).
Llach, F. et al. *Internal Medicine*, Stein, J. H. et al. ed. (Mosby, St. Louis), pp. 2609–2614 (1994).
Albert, S. et al. *Internal Medicine*, Stein, J. H. et al. ed. (Mosby, St. Louis), pp. 2765–2773 (1994).
Nordlund, J. J. et al. *Internal Medicine*, Stein, J. H. et al. ed. (Mosby, St. Louis), pp. 919–921 (1994).
Katritzky, A. R., et al. *Handbook of Heterocyclic Chemistry* (Pergamon Press, Oxford), pp. 148, 151, 167, 174, 195, 298, 307, 317, and 318 (1985).
Gilchrist, T. L. *Heterocyclic Chemistry* (Longman Scientific & Technical, Essex, England), pp. 302, 346, 347 (1992).
Gilchrist, T. L. *Aromatic and Heteroaromatic Chemistry*, vol. 4, edited by Bird, C. W. et al. (Chemical Society, London) p. 363 (1976).
Gilchrist, T. L. *Aromatic and Heteroaromatic Chemistry*, vol. 2, edited by Bird, C. W. et al. (Chemical Society, London) pp. 373, 375, and 379 (1974).
Martin, L. et al. *Internal Medicine* (Mosby, St. Louis) edited by Stein, J. H., p. 2349 (1994).
Salmon, S. E. et al. *Basic & Clinical Pharmacology*, edited by Katzung, B. G. (Appleton & Lange, Norwalk) p. 824 (1995).

*Primary Examiner*—Mukund J. Shah
*Assistant Examiner*—King Lit Wong
*Attorney, Agent, or Firm*—Oblon, Spivak, McClelland, Maier & Neustadt, P.C.

[57] ABSTRACT

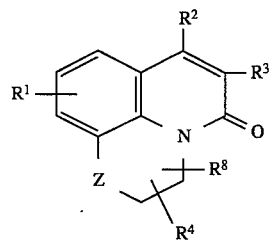

wherein $R^1$ is hydrogen, lower alkyl, lower alkoxy, lower alkylthio, halogen, nitro, amino or protected amino, $R^2$ is hydroxy, protected hydroxy, halogen, amino or protected amino, $R^3$ is hydrogen or an organic group, $R^4$ R is hydrogen or lower alkyl, $R^8$ is hydrogen or lower alkyl, and —Z— is —O— or a group of the formula:

$$-\underset{(O)_n}{S}-$$

(in which n is 0, 1 or 2),
and pharmaceutically acceptable salts thereof which are useful as a medicament.

9 Claims, No Drawings

HETEROTRICYCLIC DERIVATIVES, PROCESS FOR THEIR PREPARATION AND PHARMACEUTICAL COMPOSITIONS CONTAINING THEM

TECHNICAL FIELD

This relates to new heterotricyclic derivatives and pharmaceutically acceptable salts thereof which are useful as a medicament.

BACKGROUND ART

Some heterotricyclic derivatives have been known as described, for example, in U.S. Pat. No. 4,547,511.

DISCLOSURE OF INVENTION

This invention relates to new heterotricyclic derivatives. More particularly, this invention relates to new heterotricyclic derivatives and pharmaceutically acceptable salts thereof which have pharmacological activities, processes for preparation thereof, a pharmaceutical composition comprising the same and a use of the same.

Accordingly, one object of this invention is to provide the new and useful heterotricyclic derivatives and pharmaceutically acceptable salts thereof which possess a strong immunomodulating activity (e.g. an inhibitory activity on the production of an autoantibody, etc.), anti-inflammatory activity and anti-cancer activity.

Another object of this invention is to provide processes for preparation of the heterotricyclic derivatives and salts thereof.

A further object of this invention is to provide a pharmaceutical composition comprising said heterotricyclic derivatives or a pharmaceutically acceptable salt thereof.

Still further object of this invention is to provide a use of said heterotricyclic derivatives or a pharmaceutically acceptable salt thereof as a medicament for the treatment and/or prevention of inflammatory conditions, various pains, collagen diseases, auto-immune diseases, various immunity diseases, cancer and the like in human being and animals.

The object heterotricyclic derivatives of the present invention are novel and can be represented by the following general formula (I):

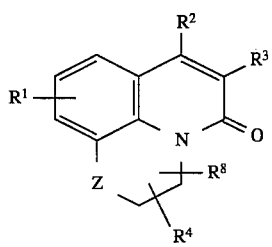

wherein $R^1$ is hydrogen, lower alkyl, lower alkoxy, lower alkylthio, halogen, nitro, amino or protected amino, $R^2$ is hydroxy, protected hydroxy, halogen, amino or protected amino, $R^3$ is hydrogen or an organic group, $R^4$ is hydrogen or lower alkyl, $R^8$ is hydrogen or lower alkyl, and —Z— is —O— or a group of the formula:

(in which n is 0, 1 or 2).

The object compound (I) of the present invention can be prepared by the following processes.

Process (1)

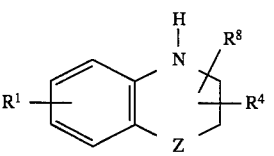

(II)
or a salt thereof

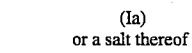

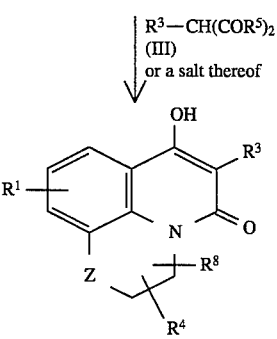

(Ia)
or a salt thereof

Process (2)

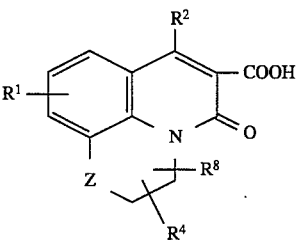

(Ib)
or its reactive derivative
at the carboxy group, or a salt thereof

↓ Amidation reaction

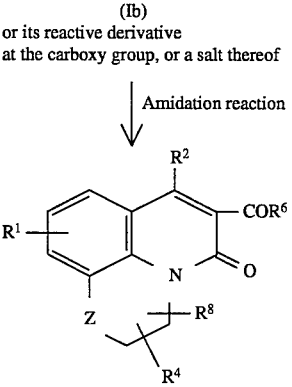

(Ic)
or a salt thereof

Process (3)
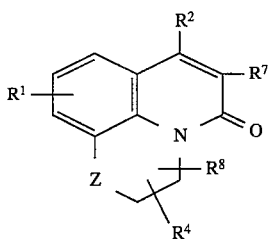
(IV) or a salt thereof
↓ Elimination reaction of the carboxy protective group
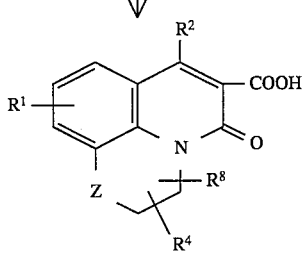
(Ib) or a salt thereof
Process (4)
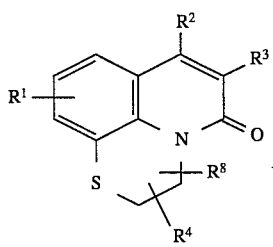
(Id) or a salt thereof
↓ oxidation
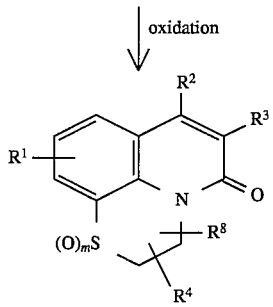
(Ie) or a salt thereof
Process (5)
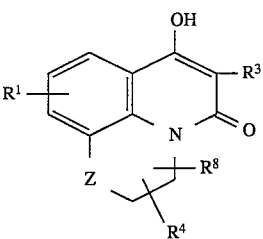
(Ia) or a salt thereof
① ↓ halogenation
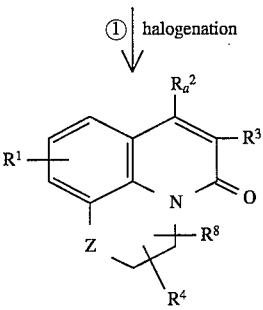
(Ih) or a salt thereof
② ↓ amination
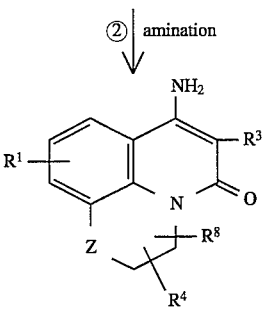
(Ii) or a salt thereof
Process (6)
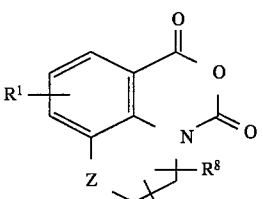
(VII) or a salt thereof
↓ $R^9-\overset{O}{\underset{\|}{C}}-CH_2-R^3$
(VI) or a salt thereof

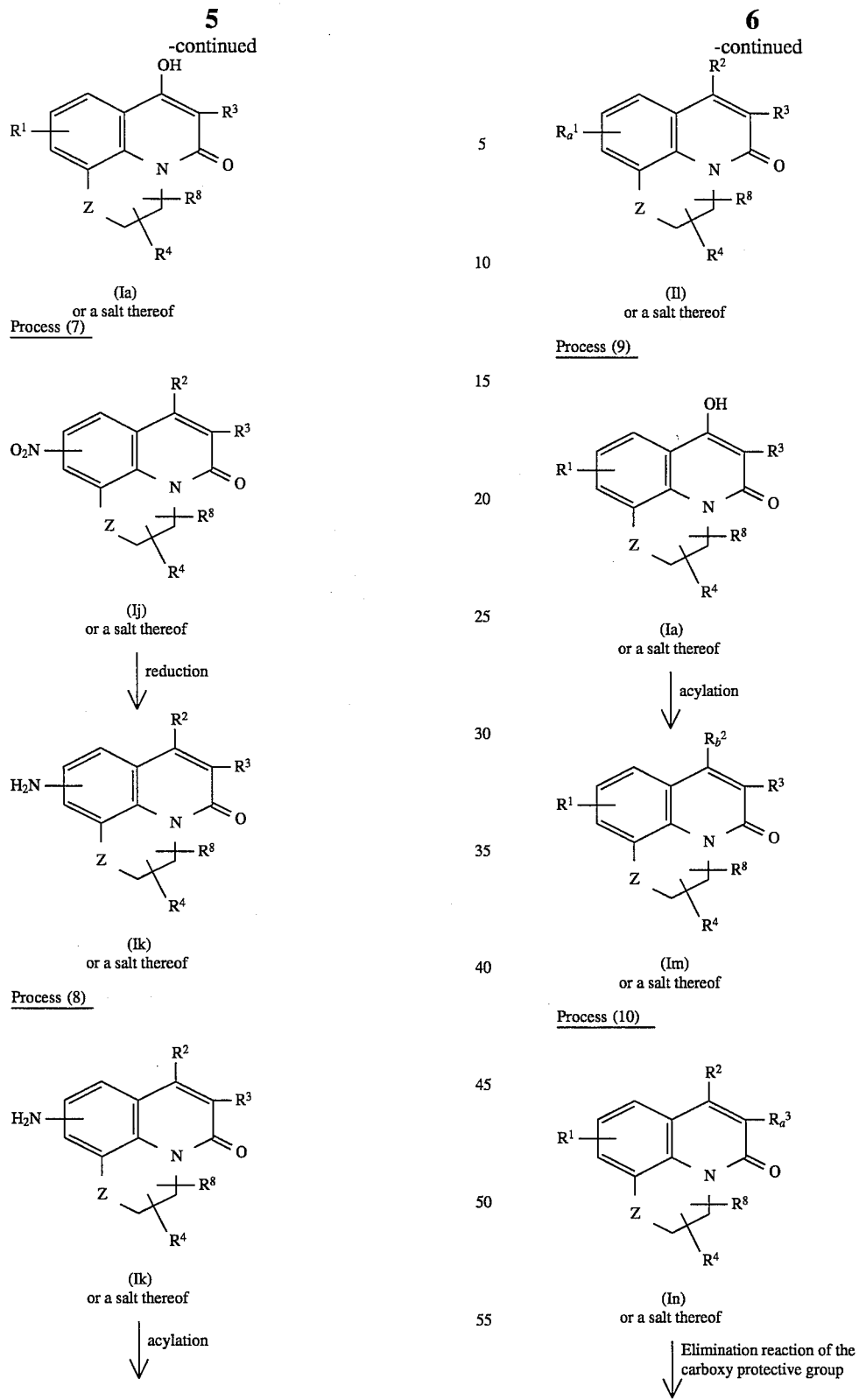

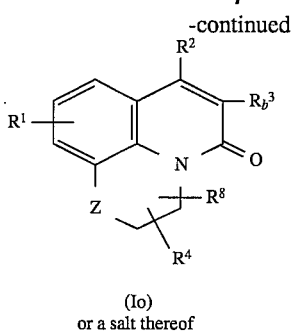

(Io)
or a salt thereof

Process (11)

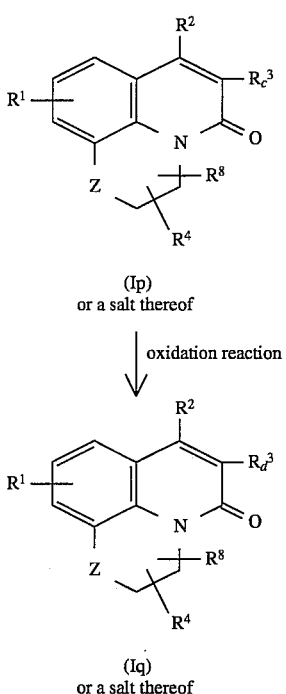

wherein $R^1$, $R^2$, $R^3$, $R^4$, $R^8$ and —Z— are each as defined above, $R^1_a$ is acylamino, $R_a$ is halogen, $R_{b3}$ is acyloxy, $R_a$ is acyl having protected carboxy, $R_{b3}$ is acyl having carboxy, $R_c$ is acyl having lower alkylsulfinyl or lower alkylsulfonyl, $R^5$ and $R^9$ are each a leaving group, a group of the formula: —$COR^6$ is amidated carboxy, $R^7$ is protected carboxy, and m is 1 to 2.

Suitable pharmaceutically acceptable salts of the object compound (I) are conventional non-toxic salts and may include e.g. a salt with a base or an acid addition salt such as a salt with an inorganic base, for example, an alkali metal salt (e.g. sodium salt, potassium salt, etc.), an alkaline earth metal salt (e.g. calcium salt, magnesium salt, etc.), an ammonium salt; a salt with an organic base, for example, an organic amine salt (e.g. triethylamine salt, pyridine salt, picoline salt, ethanolamine salt, triethanolamine salt, dicyclohexylamine salt, N,N'-dibenzylethylenediamine salt, etc.); an inorganic acid addition salt (e.g. hydrochloride, hydrobromide, sulfate, phosphate, etc.); an organic carboxylic or sulfonic acid addition salt (e.g. formate, acetate, trifluoroacetate, maleate, tartrate, methanesulfonate, benzenesulfonate, toluenesulfonate, etc.); a salt with a basic or acidic amino acid (e.g. arginine, aspartic acid, glutamic acid, etc.).

In the above and subsequent descriptions of the present specification, suitable example and illustration of the various definitions which the present invention intends to include within the scope thereof are explained in detail as follows.

The term "lower" is used to intend a group having 1 to 6, preferably 1 to 4, carbon atom (s), unless otherwise provided.

The term "higher" is used to intend a group having 7 to 20 carbon atoms, unless otherwise provided.

Suitable "lower alkyl" and "lower alkyl moiety" in the terms "lower alkylthio" "ower alkylsulfinyl" and "lower alkylsulfonyl" may include straight or branched one such as methyl, ethyl, propyl, isopropyl, butyl, t-butyl, pentyl, hexyl, and the like, in which more preferable example may be $C_1$–$C_4$ alkyl.

Suitable "lower alkoxy" may include methoxy, ethoxy, propoxy, isopropoxy, butoxy, isobutoxy, t-butoxy, pentyloxy, t -pentyloxy, hexyloxy and the like, in which more preferable example may be $C_1$–$C_4$ alkoxy.

Suitable "halogen" may include fluorine, chlorine, bromine and iodine.

Suitable "protected hydroxy" may be acyloxy group or the like.

Suitable "protected amino" may include acylamino and the like.

Suitable "acyl moiety" in the terms "acyloxy" and "acylamino" may include carbamoyl, aliphatic acyl group and acyl group containing an aromatic ring, which is referred to as aromatic acyl, or heterocyclic ring, which is referred to as heterocyclic acyl.

Suitable example of said acyl may be illustrated as follows:—Carbamoyl;

Aliphatic acyl such as lower or higher alkanoyl (e.g. formyl, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl, icosanoyl, etc.);

lower or higher alkoxycarbonyl (e.g. methoxycarbonyl, ethoxycarbonyl, t-butoxycarbonyl, t-pentyloxycarbonyl, heptyloxycarbonyl, etc.);

lower or higher alkylsulfonyl (e.g. methylsulfonyl, ethylsulfonyl, etc.);

lower or higher alkoxysulfonyl (e.g. methoxysulfonyl, ethoxysulfonyl, etc.); or the like;

Aromatic acyl such as aroyl (e.g. benzoyl, toluoyl, naphthoyl, etc.);

ar(lower)alkanoyl [e.g. phenyl(lower)alkanoyl (e.g. phenylacetyl, phenylpropanoyl, phenylbutanoyl, phenylisobutylyl, phenylpentanoyl, phenylhexanoyl, etc.), naphthyl(lower)alkanoyl (e.g. naphthylacetyl, naphthylpropanoyl, naphthylbutanoyl, etc.)];

ar(lower)alkenoyl [e.g. phenyl(lower)alkenoyl (e.g. phenylpropenoyl, phenylbutenoyl, phenylmethacryloyl, phenylpentenoyl, phenylhenxenoyl, etc.), naphthyl(lower)alkenoyl (e.g. naphthylpropenoyl, naphthylbutenoyl, naphthylpentenoyl, etc.), etc.];

ar(lower)alkoxycarbonyl [e.g. phenyl(lower)alkoxycarbonyl (e.g. benzyloxycarbonyl, etc.), etc.];

aryloxycarbonyl (e.g. phenoxycarbonyl, naphthyloxycarbonyl, etc.);

aryloxy(lower)alkanoyl (e.g. phenoxyacetyl, phenoxypropionyl, etc.);

arylglyoxyloyl (e.g. phenylglyoxyloyl, naphthylglyoxyloyl, etc.);

arenesulfonyl (e.g. benzenesulfonyl, p-toluenesulfonyl, etc.); or the like;

Heterocyclic acyl such as heterocycliccarbonyl; heterocyclic(lower)alkanoyl (e.g. thienylacetyl, thienylpropanoyl, thienylbutanoyl, thienylpentanoyl, thienylhexanoyl, thiazolylacetyl, thiadiazolylacetyl, tetrazolylacetyl, etc.);

heterocyclic(lower)alkenoyl (e.g. heterocyclicpropenoyl, heterocyclicbutenoyl, heterocyclicpentenoyl, heterocyclichexenoyl, etc.);

heterocyclicglyoxyloyl (e.g. thiazolylglyoxyloyl, thienylglyoxyloyl, etc.); or the like; in which suitable heterocyclic moiety in the terms "heterocycliccarbonyl", "heterocyclic(lower)alkanoyl", heterocyclic(lower)alkenoyl and "heterocyclicglyoxyloyl" as mentioned above means, in more detail, saturated or unsaturated, monocyclic or polycyclic heterocyclic group containing at least one heteroatom such as an oxygen, sulfur, nitrogen atom and the like.

And especially preferable heterocyclic group may be heterocyclic group such as unsaturated 3 to 8-membered (more preferably 5 or 6-membered) heteromonocyclic group containing 1 to 4-nitrogen atom(s), for example, pyrrolyl, pyrrolinyl, imidazolyl, pyrazolyl, pyridyl and its N-oxide, dihydropyridyl, pyrimidyl, pyrazinyl, pyridazinyl, triazolyl (e.g. 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), etc.;

saturated 3 to 8-membered (more preferably 5 or 6-membered) heteromonocyclic group containing 1 to 4 nitrogen atom(s), for example, pyrrolidinyl, imidazolidinyl, piperidyl, piperazinyl, etc.;

unsaturated condensed heterocyclic group containing 1 to 4 nitrogen atom(s), for example, indolyl, isoindolyl, indolinyl, indolizinyl, benzimidazolyl, quinolyl, tetrahydroquinolyl, (e.g. 1,2,3,4-tetrahydroquinolyl, etc.), isoquinolyl, tetrahydroisoquinolyl, (e.g. 1,2,3,4-tetrahydroisoquinolyl, etc.), indazolyl, quinoxalinyl, tetrahydroquinoxalinyl (e.g. 1,2,3,4-tetrahydroquinoxalinyl, etc.), benzotriazolyl, etc.;

unsaturated 3 to 8-membered (more preferably 5 or 6-membered) heteromonocyclic group containing 1 to 2 oxygen atom(s) and 1 to 3 nitrogen atom(s), for example, oxazolyl, isoxazolyl, oxadiazolyl (e.g. 1,2,4-oxadiazolyl, 1,3,4-oxadiazolyl, 1,2,5-oxadiazolyl, etc.) etc.;

saturated 3 to 8-membered (more preferably 5 or 6-membered) heteromonocyclic group containing 1 to 2 oxygen atom(s) and 1 to 3 nitrogen atom(s), for example, morpholinyl, syndonyl, etc.;

unsaturated condensed heterocyclic group containing 1 to 2 oxygen atom(s) and 1 to 3 nitrogen atom(s), for example, benzoxazolyl, benzoxadiazolyl, benzoxazinyl (e.g., 2H-1,4-benzoxaziny1,4H-1,4-benzoxazinyl, etc.), dihydrobenzoxazinyl (e.g., 3,4-dihydro-2H-1,4benzoxazinyl, etc.), etc.;

unsaturated 3 to 8-membered (more preferably 5 or 6-membered) heteromonocyclic group containing 1 to 2 sulfur atom(s) and 1 to 3 nitrogen atom(s), for example, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.), dihydrothiazinyl, etc.;

saturated 3 to 8-membered (more preferably 5 or 6-membered) heteromonocyclic group containing 1 to 2 sulfur atom(s) and 1 to 3 nitrogen atom(s), for example, thiazolidinyl, etc.;

unsaturated 3 to 8-membered (more preferably 5 or 6-membered) heteromonocyclic group containing 1 to 2 sulfur atom(s), for example, thienyl, dihydrodithiinyl, dihydrodithionyl, etc.; unsaturated condensed heterocyclic group containing 1 to 2 sulfur atom(s) and 1 to 3 nitrogen atom(s), for example, benzothiazolyl, benzothiadiazolyl, benzothiazinyl (e.g., 2H-1,4-benzothiazinyl, 4H-1,4-benzothiazinyl, etc.), dihydrobenzothiazinyl (e.g., 3,4-dihydro-2H-1,4benzothiazinyl, etc.), etc.;

unsaturated 3 to 8-membered (more preferably 5 or 6-membered) heteromonocyclic group containing an oxygen atom, for example, furyl, etc.;

unsaturated 3 to 8-membered (more preferably 5 or 6-membered) heteromonocyclic group containing an oxygen atom and 1 to 2 sulfur atom(s), for example, dihydrooxathiinyl, etc.;

unsaturated condensed heterocyclic group containing 1 to 2 sulfur atom(s), for example, benzothienyl, benzodithiinyl, etc.;

unsaturated condensed heterocyclic group containing an oxygen atom and 1 to 2 sulfur atom(s), for example, benzoxathiinyl, etc. and the like.

The acyl as stated above may have one to ten, same or different, suitable substituent(s) such as halogen, carboxy, protected carboxy, hydroxy, protected hydroxy, nitro, lower alkyl, heterocyclic group, cyclo(lower)alkyl, ar(lower)alkyl, lower alkoxy, aryl which may have suitable substituent(s), or the like.

Suitable "organic group" may include lower alkyl, lower alkenyl, lower alkynyl, aryl, ar(lower)alkyl, carboxy, acyl as exemplified above, and the like.

Suitable "leaving group" may include lower alkoxy (e.g. methoxy, ethoxy, propoxy, isopropoxy, butoxy, isobutoxy, t-butoxy, pentoxy, etc.), aryloxy (e.g. phenoxy, napthoxy, etc.), an acid residue or the like, and suitable examples of "acid residue" may be halogen (e.g. chlorine, bromine, iodine, etc.), sulfonyloxy (e.g. methanesulfonyloxy, benzenesulfonyloxy, toluenesulfonyloxy, etc.) or the like.

Suitable "amidated carboxy" may include carbamoyl which may have one or two suitable substituent(s) a group (wherein a group of the formula: —CO—N

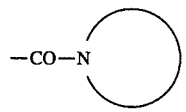

(wherein a group of the formula: —N

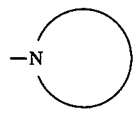

is a heterocyclic group containing at least one nitrogen atom which may have suitable substituent(s)), and the like.

Suitable "lower alkyl moiety" in the term "ar(lower)alkyl" can be referred to the ones as mentioned above.

Suitable "lower alkenyl" may include vinyl, 1-propenyl, allyl, 1-methylallyl, 1 or 2 or 3-butenyl, 1 or 2 or 3 or 4-pentenyl, 1 or 2 or 3 or 4 or 5-hexenyl and the like.

Suitable "lower alkynyl" may include ethynyl, 1-propynyl, propargyl, 1-methylpropargyl, 1 or 2 or 3 butynyl, 1 or 2 or 3 or 4-pentynyl, 1 or 2 or 3 or 4 or 5-hexynyl and the like.

Suitable "substituent" in the term "carbamoyl which may have one or two suitable substituent(s)" may include lower alkyl, heterocyclic group, cyclo(lower)alkyl, aryl which may have suitable substituent(s), ar(lower)alkyl and the like.

Suitable "aryl" and "aryl moiety" in the term "ar(lower)alkyl" may include phenyl, naphthyl and the like.

Suitable "substituent" in the term "aryl which may have suitable substituent(s)" may include lower alkylthio, halogen, lower alkylsulfinyl, acyl as exemplified above and the like.

Suitable "cyclo(lower)alkyl" may include 3 to 8-membered cycloalkyl such as cyclopropyl, cyclobutyl, cyclopentyl, cyclohexyl, cycloheptyl, cyclooctyl, and the like.

Suitable "heterocyclic group" can be referred to the ones as mentioned above.

Suitable "protected carboxy" may include esterified carboxy and the like. An suitable examples of said ester moiety may be the ones such as lower alkyl ester (e.g., methyl ester, ethyl ester, propyl ester, isopropyl ester, butyl ester, isobutyl ester, t-butyl ester, pentyl ester, t-pentyl ester, hexyl ester, 1-cyclopropylethyl ester, etc.);

lower alkenyl ester (e.g., vinyl ester, allyl ester, etc.);

lower alkynyl ester (e.g., ethynyl ester, propynyl ester, etc.);

lower alkoxyalkyl ester (e.g., methoxymethyl ester, ethoxymethyl ester, isopropoxymethyl ester, 1-methoxyethyl ester, 1-ethoxyethyl ester, etc.);

lower alkylthioalkyl ester (e.g., methylthiomethyl ester, ethylthiomethyl ester, ethylthioethyl ester, isopropylthiomethyl ester, etc.);

mono(or di or tri)halo(lower)alkyl ester (e.g. 2-iodoethyl ester, 2,2,2-trichloroethyl ester, etc.);

lower alkanoyloxy(lower)alkyl ester (e.g., acetoxymethyl ester, propionyloxymethyl ester, butyryloxymethyl ester, valeryloxymethyl ester, pivaloyloxymethyl ester, hexanoyloxymethyl ester, 2-acetoxyethyl ester, 2-propionyloxyethyl ester, etc.);

lower alkanesulfonyl(lower)alkyl ester (e.g. mesylmethyl ester, 2-mesylethyl ester etc.);

ar(lower)alkyl ester, for example, phenyl(lower)alkyl ester which may have one or more suitable substituent(s) (e.g., benzyl ester, 4-methoxybenzyl ester, 4-nitrobenzyl ester, phenethyl ester, trityl ester, benzhydryl ester, bis-(methoxyphenyl)methyl ester, 3,4-dimethoxybenzyl ester, 4-hydroxy-3,5-di-t-butylbenzyl ester, etc.);

aryl ester which may have one or more suitable substituent(s) such as substituted or unsubstituted phenyl ester (e.g., phenyl ester, tolyl ester, t-butylphenyl ester, xylyl ester, mesityl ester, cumenyl ester, 4-chlorophenyl ester, 4-methoxyphenyl ester, etc.);

tri(lower)alkyl silyl ester; lower alkylthioester (e.g. methylthioester, ethylthioester, etc.) and the like.

Suitable "heterocyclic group containing at least one nitrogen atom" may include unsaturated 3 to 8-membered (more preferably 5 or 6-membered) heteromonocyclic group containing 1 to 4-nitrogen atom(s), for example, pyrrolyl, pyrrolinyl, imidazolyl, pyrazolyl, dihydropyridyl, triazolyl (e.g. 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), etc.;

saturated 3 to 8-membered (more preferably 5 or 6-membered) heteromonocyclic group containing 1 to 4 nitrogen atom(s), for example pyrrolidinyl, imidazolidinyl, piperidyl, piperazinyl, etc.;

unsaturated condensed heterocyclic group containing 1 to 4 nitrogen atom(s), for example, indolyl, isoindolyl, indolinyl, benzimidazolyl, indazolyl, benzotriazolyl, tetrahydroquinolyl (e.g., 1,2,3,4-tetrahydroquinolyl, etc.), tetrahydroisoquinolyl (e.g., 1,2,3,4-tetrahydroisoquinolyl, etc.), tetrahydroquinoxalinyl (e.g., 1,2,3,4-tetrahydroquinoxalinyl, etc.), etc.;

saturated 3 to 8-membered (more preferably 5 or 6-membered) heteromonocyclic group containing 1 to 2 oxygen atom(s) and 1 to 3 nitrogen atom(s), for example, morpholinyl, etc.;

unsaturated condensed heterocyclic group containing 1 to 2 oxygen atom(s) and 1 to 3 nitrogen atom(s), for example, benzoxazolyl, benzoxadiazolyl, benzoxazinyl (e.g., 4H-1,4-benzoxazinyl, etc.), dihydrobenzoxazinyl (e.g., 3,4-dihydro-2H-1,4-benzoxazinyl, etc.), etc.; unsaturated 3 to 8-membered (more preferably 5 or -membered) heteromonocyclic group containing 1 to 2 sulfur atom(s) and 1 to 3 nitrogen atom(s), for example, dihydrothiazinyl, etc.;

unsaturated condensed heterocyclic group containing 1 to 2 sulfur atom(s) and 1 to 3 nitrogen atom(s), for example, benzothiazolyl, benzothiadiazolyl, benzothiazinyl (e.g., H-1,4-benzothiazinyl, etc.), dihydrobenzothiazinyl (e.g. 3,4-dihydro-2H-1,4-benzothiazinyl, etc.), etc.;

saturated 3 to 8-membered (more preferably 5 or 6-membered) heteromonocyclic group containing 1 to 2 sulfur atom(s) and 1 to 3 nitrogen atom(s), for example, thiazolidinyl, etc.; and the like.

Suitable "substituent" in the term "heterocyclic group containing at least one nitrogen atom which may have suitable substituent(s)" may include halogen, hydroxy, protected hydroxy, nitro, lower alkyl, lower alkoxy, carboxy, protected carboxy and the like.

The processes for preparing the object and starting compounds are explained in detail in the following.

Process (1)

The object compound (Ia) or a salt thereof can be prepared by reacting the compound (II) or a salt thereof with the compound (III) or a salt thereof.

The reaction is usually carried out in a conventional solvent such as chloroform, ether, tetrahydrofuran, diphenyl ether, benzene, N,N-dimethylformamide, N,N-dimethylacetamide or any other organic solvent which does not adversely influence the reaction.

When the starting compounds are in liquid, they can be used also as a solvent.

The reaction temperature is not critical and the reaction is usually carried out under warming to heating.

Process (2)

The compound (Ic) or a salt thereof can be prepared by subjecting the compound (Ib) or its reactive derivative at the carboxy group, or a salt thereof to amidation reaction.

Suitable amidating reagent to be used in the present amidation reaction may include a compound of the formula:

H—R⁶       (V)

(wherein $R^6$ is as defined above)
or its reactive derivative or a salt thereof, and the like.

Suitable reactive derivative of the compound (V) may include Schiff's base type imino or its tautomeric enamine type isomer formed by the reaction of the compound (V) with a carbonyl compound such as aidehyde, ketone or the like; a silyl derivative formed by the reaction of the compound (V) with a silyl compound such as bis(trimethylsilyl)acetamide, mono(trimethylsilyl)acetamide [e.g. N-(trimethylsilyl)acetamide], bis(trimethylsilyl)urea or the like; a derivative formed by reaction of the compound (V) with phosphorus trichloride or phosgene, and the like.

Suitable reactive derivative at the carboxy group of the compound (Ib) may include an acid halide, an acid anhydride, an activated amide, an activated ester, and the like. Suitable examples of the reactive derivatives may be an acid chloride; an acid azide; a mixed acid anhydride with an acid such as substituted phosphoric acid [e.g. dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g. methanesulfonic acid, etc.], aliphatic carboxylic acid [e.g. acetic acid, propionic acid, butyric acid, isobutyric acid, pivalic acid, pentanoic acid, isopentanoic acid, 2-ethylbutyric acid, trichloroacetic acid, etc.] or aromatic carboxylic acid [e.g. benzoic acid, etc.]; a symmetrical acid anhydride; an activated amide with imidazole, 4-substituted imidazole, dimethylpyrazole, triazole or tetrazole; or an activated ester [e.g. cyanomethyl ester, methoxymethyl ester, dimethyliminomethyl

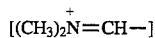

ester, vinyl ester, ethyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.], or an ester with a N-hydroxy compound [e.g. N,N-dimethyl hydroxylamine, 1-hydroxy-2-(1H)-pyridone, N-hydroxysuccinimide, N-hydroxyphthalimide, 1-hydroxy-1H-benzotriazole, etc.], and the like. These reactive derivatives can optionally be selected from them according to the kind of the compound (Ib) to be used.

The reaction is usually carried out in a conventional solvent such as water, dioxane, acetonitrile, chloroform, methylene chloride, ethylene chloride, tetrahydrofuran, toluene, ethyl acetate, N,N-dimethylformamide, pyridine or any other organic solvent which does not adversely influence the reaction. These conventional solvent may also be used in a mixture with water. When the base and/or the starting compound are in liquid, they can be used also as a solvent.

In this reaction, when the compound (Ib) is used in a free acid form or its salt form, the reaction is preferably carried out in the presence of a conventional condensing agent such as N,N'-dicyclohexylcarbodiimide; N-cyclohexyl-N'-morpholinoehtylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N'-carbonyl-bis(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; thionyl chloride; oxalyl chloride; lower alkyl haloformate [e.g. ethyl chloroformate, isopropyl chloroformate, etc.]; triphenylphosphine; 2-ethyl-7-hydroxybenzisoxazolium salt; 2-ethyl-5-(m-sulfophenyl)isoxazolium hydroxide intramolecular salt; 1-(p-chlorobenzenesulfonyloxy)-6-chloro-1H-benzotriazole; so-called Viismeier reagent prepared by the reaction of N,N-dimethylformamide with thionyl chloride, phosgene, trichloromethyl chloroformate, phosphorus oxychloride, etc.; or the like.

The reaction may also be carried out in the presence of an organic base such as tri(lower)alkylamine, pyridine, N-(lower)alkylmorpholine, N,N-di(lower)alkylbenzylamine, or the like.

The reaction temperature is not critical, and the reaction is usually carried out under cooling to heating.

Process (3)

The compound (Ib) or a salt thereof can be prepared by subjecting the compound (IV) or a salt thereof to elimination reaction of the carboxy protective group.

This reaction is carried out in accordance with a conventional method such as hydrolysis, reduction or the like.

The hydrolysis is preferably carried out in the presence of a base or an acid including Lewis acid. Suitable base may include an inorganic base and an organic base such as an alkali metal [e.g. sodium, potassium, etc.], an alkaline earth metal [e.g. magnesium, calcium, etc.], the hydroxide or carbonate or bicarbonate thereof, trialkylamine [e.g. trimethylamine, triethylamine, etc.], picoline, 1,5-diazabicyclo [4.3.0]non-5-ene, 1,4-diazabicyclo[2.2.2]octane, 1,8-diazabicyclo[5.4.0]-undec-7-ene, or the like.

Suitable acid may include an organic acid [e.g. formic acid, acetic acid, propionic acid, trichloroacetic acid, trifluoroacetic acid, etc.] and an inorganic acid [e.g. hydrochloric acid, hydrobromic acid, sulfuric acid, hydrogen chloride, hydrogen bromide, etc.]. The elimination using Lewis acid such as trihaloacetic acid [e.g. trichloroacetic acid, trifluoroacetic acid, etc.] or the like is preferably carried out in the presence of cation trapping agent [e.g. anisole, phenol, etc.].

The reaction is usually carried out in a solvent such as water, an alcohol [e.g. methanol, ethanol, etc.], methylene chloride, tetrahydrofuran, a mixture thereof or any other solvent which does not adversely affect the reaction. A liquid base or acid can be also used as the solvent. The reaction temperature is not critical and the reaction is usually carried out under cooling to warming.

The reduction method applicable for the elimination reaction may include chemical reduction and catalytic reduction.

Suitable reducing agents to be used in chemical reduction are a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid hydrobromic acid, etc.].

Suitable catalysts to be used in catalytic reduction are conventional ones such as platinum catalysts [e.g. platinum plate, spongy platinum, platinum black, colloidal platinum, platinum oxide, platinum wire, etc.], palladium catalysts [e.g. spongy palladium, palladium black, palladium oxide, palladium on carbon, colloidal palladium, palladium on barium sulfate, palladium on barium carbonate, etc.], nickel catalysts [e.g. reduced nickel, nickel oxide, Raney nickel, etc.], cobalt catalysts [e.g. reduced cobalt, Raney cobalt, etc.], iron catalysts [e.g. reduced iron, Raney iron, etc.], copper catalysts [e.g. reduced copper, Raney copper, Ullman copper, etc.] and the like.

The reduction is usually carried out in a conventional solvent which does not adversely affect the reaction such as water, methanol, ethanol, propanol, N,N-dimethylformamide, diethyl ether, dioxane, tetrahydrofuran, etc., or a mixture thereof. Additionally, in case that the above-mentioned acids to be used in chemical reduction are in liquid, they can also be used as a solvent.

The reaction temperature of this reduction is not critical and the reaction is usually carried out under cooling to heating.

Process (4)

The compound (Ie) or a salt thereof can be prepared by subjecting the compound (Id) or a salt thereof to oxidation reaction.

Oxidation is carried out in a conventional manner, which is capable of oxidizing a sulfur atom to an oxidized sulfur atom, and suitable oxidizing reagent may be oxygen acid such as periodate (e.g. sodium periodate, potassium periodate, etc.), peroxy acid such as peroxybenzoic acids (e.g. peroxybenzoic acid, m-chloroperoxybenzoic acid, etc.), and the like.

The reaction is usually carried out in a conventional solvent such as water, alcohol (e.g., methanol, ethanol, isopropyl alcohol, etc.), tetrahydrofuran, dioxane, dichloromethane, chloroform, N,N-dimethyl acetamide, N,N-dimethylformamide or any other organic solvent which does not adversely influence the reaction. Among these solvents, hydrophilic solvents may be used in a mixture with water.

The reaction temperature is not critical and the reaction is usually carried out under cooling to heating.

Process (5)-①

The compound (Ih) or a salt thereof can be prepared by subjecting the compound (Ia) or a salt thereof to halogenation reaction.

This reaction can be carried out in the manner disclosed in Example 19 or similar manners thereto.

Process (5)-②

The compound (Ii) or a salt thereof can be prepared by subjecting the compound (Ih) or a salt thereof to amination reaction.

This reaction can be carried out in the manner disclosed in Example 20 or similar manners thereto.

Process (6)

The compound (Ia) or a salt thereof can be prepared by reacting the compound (VII) or a salt thereof with the compound (VI) or a salt thereof.

This reaction is usually carried out in a solvent such as water, alcohol (e.g., methanol, ethanol, etc.), benzene, N,N-dimethylformamide, tetrahydrofuran, toluene, methylene chloride, ethylene dichloride, chloroform, dioxane, diethyl ether or any other solvent which does not adversely affect the reaction. These conventional solvent may also be used in a mixture with water.

The reaction temperature is not critical and the reaction is usually carried out under cooling to heating.

The reaction is usually carried out in the presence of an inorganic or an organic base such as an alkali metal (e.g., sodium, potassium, etc.), an alkali metal hydroxide (e.g., sodium hydroxide, potassium hydroxide, etc.), an alkali metal hydrogencarbonate (e.g., sodium hydrogencarbonate, potassium hydrogencarbonate, etc.), alkali metal carbonate (e.g., sodium carbonate, potassium carbonate, etc.), tri(lower)alkylamine (e.g., trimethylamine, triethylamine, diisopropylethylamine, etc.), alkali metal hydride (e.g., sodium hydride, etc.), alkali metal (lower)alkoxide (e.g., sodium methoxide, sodium ethoxide, etc.), pyridine, lutidine, picoline, dimethylaminopyridine, N-(lower)alkylmorpholine, N,N-di(lower)alkylbenzylamine, N,N-di(lower)alkylaniline or the like.

When the base and/or the starting compound are in liquid, they can be also used as a solvent.

Process (7)

The compound (Ik) or a salt thereof can be prepared by subjecting the compound (Ij) or a salt thereof to reduction reaction.

This reaction can be carried out in the manners disclosed in Examples 22 and 23 or similar manners thereto.

Process (8)

The compound (Il) or a salt thereof can be prepared by subjecting the compound (Ik) or a salt thereof to acylation reaction.

This reaction can be carried out in the manner disclosed in Example 24 or similar manners thereto.

Process (9)

The compound (Im) or a salt thereof can be prepared by subjecting the compound (Ia) or a salt thereof to acylation reaction.

This reaction can be carried out in the manner disclosed in Example 23 or similar manners thereto.

Process (10)

The compound (Io) or a salt thereof can be prepared by subjecting the compound (In) or a salt thereof to elimination reaction of the carboxy protective group.

This reaction can be carried out in a similar manner to that of the aforementioned process (3), and therefore the reagents to be used and the reaction conditions (e.g., solvent, reaction temperature, etc.) can be referred to those of the Process (3).

Process (11)

The compound (Iq) or a salt thereof can be prepared by subjecting the compound (Ip) or a salt thereof to oxidation reaction.

This reaction can be carried out in a similar manner to that of the aforementioned Process (4), and therefore the regents to be used and the reaction conditions (e.g., solvent, reaction temperature, etc.) can be referred to those of the Process (4).

Suitable salts of the object and starting compounds and their reactive derivatives in Processes (1)∝(11) can be referred to the ones as exemplified for the compound (I).

The new heterotricyclic derivatives (I) and a pharmaceutically acceptable salt thereof of the present invention possess a strong immunomodulating activity (e.g. an inhibitory activity on the production of an autoantibody, etc.), anti-inflammatory activity, and anti-cancer activity, and therefore are useful as an immunomodulating agent (e.g. an inhibitor on the production of an autoantibody, etc.), anti-inflammatory agent and anti-cancer agent.

Accordingly, the new heterotricyclicderivatives (I) and a pharmaceutically acceptable salt thereof can be used 10 for the treatment and/or prevention of inflammatory conditions, various pains, collagen diseases, auto-immune diseases, various immunity diseases and the like in human beings of animals, and more particularly for the treatment and/or prevention of inflammation and pain in joint and muscle [e.g. rheumatoid arthritis, rheumatoid spondylitis, osteoarthritis, gouty arthritis, etc.], inflammatory skin condition [e.g. sunburn, eczema, etc.], inflammatory eye condition

[e.g. conjunctivitis etc.], lung disorder in which inflammation is involved [e.g. asthma, bronchitis, pigeon fancier's disease, farmer's lung, etc.], condition of the gastrointestinal tract associated with inflammation [e.g. aphthous ulcer, Crohn's disease, atrophic gastritis, gastritis varialoforme, ulcerative colitis, coeliac disease, regional ileitis, irritable bowel syndrome, etc.], gingivitis, (inflammation, pain and tumescence after operation or injury), pyrexia, pain and other conditions associated with inflammation, rejection by transplantation, systemic lupus erythematosus, scleroderma, polymyositis, polychondritis, periarteritis nodosa, ankylosing spondytis, inflammatory chronic renal condition [e.g. glomerulonephritis, membranous nephritis, etc.], rheumatic fever, sjëgren's syndorome, Behcet disease, thyroiditis, type I diabetes, dermatomyositis, chronic active hepatitis, myasthenia gravis, idiopathic sprue, Grave's disease, multiple sclerosis, primary billiary cirrhoris, Reiter's syndrome, autoimmune hematological disorders [e.g. hemolytic anemia, pure red cell anemia, idiopathic thrombocytopenia, aplastic anemia, etc.], myasthenia gravis, uveitis, contact dermatitis, psoriasis, Kawasaki disease, sarcoidosis, Wegner's granulomatosis, Hodgkin's disease, cancer [e.g. lung carcinoma, stomach carcinoma, colon cancer, renal carcinoma, hepatoma, etc.], and the like.

In order to show the utilities of the heterotricyclic derivatives (I) and a pharmaceutically acceptable salt thereof of the present invention, pharmacological test data of the representative compound of the heterotricyclic derivatives (I) are illustrated in the following.

Inhibitory activity on the production of an anti-DNA-antibody and on the leakage of a proteinuria.

1. Test method

Six weeks old female (578L/6×DBA/2)$F_1$ and DBA/2 mice were used. Graft-versus-host (GVH) disease was induced in (578L/6×DBA/2)$F_1$ mice with two injections of DBA/2 spleen cells given 5 days apart. Each injection contained $5 \times 10^7$ cells. From 3 days after the second cell injection, drug was administered orally once a day for 8 weeks.

As an indication of auto-immune disease, 4 weeks after the last cell injection anti-single strand DNA antibodies were measured by enzyme-linked immunosorbent assay (ELISA) using the procedure reported by T. Fujitsu et al. (International J. Immunopharmacol, 8 897 (1986)). To assess the renal disease, 8 weeks after the last cell injection proteinuria were measured. The concentration of serum albumin in the urine was determined by the single radial immunodiffusion method using rabbit anti-mouse serum albumin antiserum. Ten mice were used per group. The activity of the compound was expressed as a % inhibition of anti-DNA antibody and proteinuria.

2. Test compound 2,3-Dihydro-7-hydroxy-9-methoxy-6-(1-indolinyl-carbonyl)-5-oxo-5H-pyrido[1,2,3-de]-1,4-benzoxazine 3. Test result

| Dose | Inhibition (%) | |
|------|---|---|
| (mg/kg) | anti-DNA antibody | proteinuria |
| 32 | 86* | 99** |

*: Significantly different from control group at P<0.05
**: Significantly different from control group at P<0.01

Inhibitory activity on B16 melanoma metastases

1. Test Method

According to the experimental schedule as exemplified below, the experiment was carried out. Mouse B16 melanoma cells ($5 \times 10^5$ cells) were inoculated intravenously to 8 weeks old female (C57BL/6) mice on day 0.

The animals were sacrificed at day 16 and tumor colonies established in lung were counted in a dissection microscope.

The test compound was administered orally once a day.

Effects of test compound on tumors were assessed by the numbers of colonies compared to control.

experimental schedule

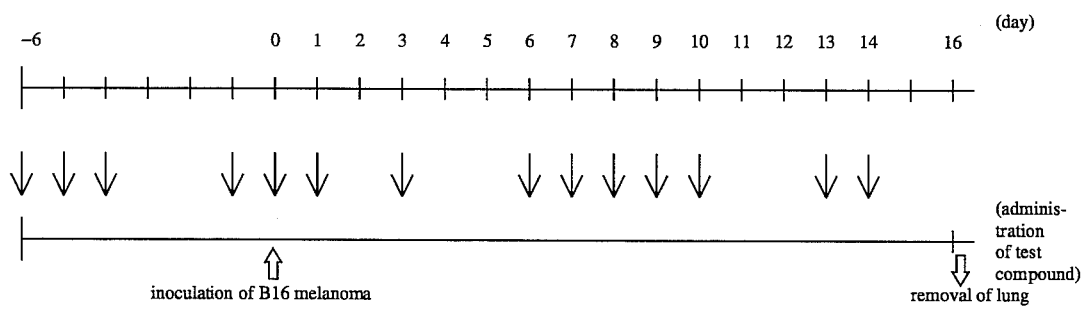

2. Test compound 2,3-Dihydro-7-hydroxy-9-methoxy-6-(1-indolinyl-carbonyl)-5-oxo-5H-pyrido[1,2,3-de]-1,4-benzoxazine 3. Test result

| Dose (mg/kg) | inhibition (%) |
|---|---|
| 32 | 36* |
| 100 | 59* |

*Significantly different from control group at P<0.01

For therapeutic administration, the object compounds (I) of the present invention and pharmaceutically acceptable salts thereof are used in a form of the conventional pharmaceutical preparation in admixture with a conventional pharmaceutically acceptable carrier such as an organic or inorganic solid or liquid excipient which is suitable for oral, parenteral or external administration. The pharmaceutical preparation may be compounded in a solid form such as granule, capsule, tablet, dragee or suppository, or in a liquid form such as solution, suspension or emulsion for injection, ingestion, eye drops, etc. If needed, there may be included in the above preparation auxiliary substance such as stabilizing agent, wetting or emulsifying agent, buffer or any other commonly used additives.

The effective ingredient may usually be administered with a unit dose of 0.01 mg/kg to 500 mg/kg, preferably 0.01 mg/kg to 10 mg/kg, 1 to 4 times a day. However, the above dosage may be increased or decreased according to age, weight and conditions of the patient or the administering method.

Preferred embodiments of the object compound (I) are as follows.

$R^1$ is hydrogen, lower alkyl, lower alkoxy, lower alkylthio, amino, protected amino [more preferably acylamino, most preferably lower alkanoylamino], halogen or nitro.

$R^2$ is hydroxy, protected hydroxy [more preferably acyloxy, most preferably lower alkanoyloxy], halogen, amino or protected amino [more preferably acylamino], $R^3$ is carboxy, or acyl [more preferably lower alkoxycarbonyl; heterocycliccarbonyl which may have one to three suitable substituent(s) [more preferably indolinylcarbonyl, tetrahydroquinolylcarbonyl, tetrahydroisoquinolylcarbonyl, tetrahydroquinoxalinylcarbonyl, dihydrobenzoxazinylcarbonyl or dihydrobenzothiazinylcarbonyl, each of which may have one to three substituent(s) selected from the group consisting of halogen, nitro, lower alkyl, lower alkoxy, carboxy and protected carboxy; most preferably indolinylcarbonyl, tetrahydroquinolylcarbonyl, tetrahydroisoquinolylcarbonyl, tetrahydroquinoxalinylcarbonyl, dihydrobenzoxazinylcarbonyl or dihydrobenzothiazinylcarbonyl, each of which may have one or two substituent(s) selected from the group consisting of halogen, nitro, lower alkyl, lower alkoxy, carboxy and esterified carboxy]; or carbamoyl which may have one or two suitable substituent(s) [more preferably carbamoyl which may have one or two substituent(s) selected from the group consisting of lower alkyl and aryl which may have one to three suitable substituent(s); most preferably carbamoyl which may have one or two substituent(s) selected from the group consisting of lower alkyl, aryl (more preferably phenyl), haloaryl (more preferably halophenyl), lower alkylthioaryl (more preferably lower alkylthiophenyl), lower alkylsulfinylaryl (more preferably lower alkylsulfinylphenyl) and acylaryl (more preferably lower alkylsulfonylphenyl)]], $R^4$ is hydrogen or lower alkyl, $R^8$ is hydrogen or lower alkyl, and —Z— is —O— or a group of the formula:

(in which n is 0, 1 or 2).

The following Examples are given for the purpose of illustrating the present invention in more detail.

EXAMPLE 1

A mixture of 3,4-dihydro-2H-1,4-benzoxazine (6 g) and tri(ethoxycarbonyl)methane (9.4 ml) was stirred at 150° C. for 1 hour and at 200° C. for 1 hour. The mixture was cooled and the solid was washed with ether to give pale brown crystals of 2,3-dihydro-6-ethoxycarbonyl-7-hydroxy-5-oxo-5H-pyrido[1,2,3-de]-1,4-benzoxazine (9.6 g).

mp: 160°–164° C. IR (Nujol): 1660, 1645, 1600, 1570 cm$^{-1}$

NMR (DMSO-d$_6$, δ): 1.30 (3H, t, J=7 Mz), 4.05 (2H, t, J=5 Mz), 4.2–4.4 (4H, m), 7.1–7.3 (2H, m), 7.62 (1H, dd, J=7.5 and 2 Mz), 13.1 (1H, s)

Mass (m/z): 275 (M$^+$), 229

EXAMPLE 2

The following compounds were obtained according to a similar manner to that of Example 1.

(1) 2,3-Dihydro-6-ethoxycarbonyl-9-fluoro-7-hydroxy-5-oxo-5H-pyrido[1,2,3-de]-1,4-benzoxazine mp: 158°–161° C.

IR (Nujol): 1650, 1570, 1500 cm$^{-1}$ NMR (CDCl$_3$, δ): 1.48 (3H, t, J=7 Mz), 4.1–4.3 (2H, m), 4.3–4.5 (2H, m), 4.51 (2H, q, J=7 Mz), 6.98 (1H, dd, J=9 and 3 Mz), 7.41 (1H, dd, J=9 and 3 Mz), 14.2 (1H, s)

Mass (m/z): 293 (M$^+$), 247

(2) 2,3-Dihydro-6-ethoxycarbonyl-7-hydroxy-9-methyl-5-oxo-5H-pyrido[1,2,3-de]-1,4-benzoxazine mp: 195°–197° C. IR (Nujol): 1670, 1570, 1495 cm$^{-1}$ NMR (CDCl$_3$, δ): 1.48 (3H, t, J=7 Mz), 2.39 (3H, s), 4.1–4.4 (4H, m), 4.49 (2H, q, J=7 Mz), 7.02 (1H, d, J=1 Hz), 7.52 (1H, d, J=1 Hz), 14.2 (1H, s)

Mass (m/z): 289 (M$^+$), 243

(3) 2,3-Dihydro-6-ethoxycarbonyl-7-hydroxy-9-methoxy-5-oxo-5H-pyrido[1,2,3-de]-1,4-benzoxazine mp: 184°–186° C.

IR (Nujol): 1645, 1570, 1490 cm$^{-1}$

NMR (CDCl$_3$, δ): 1.48 (3H, t, J=7 Mz), 3.85 (3H, s), 4.1–4.4 (4H, m), 4.45 (2H, q, J=7 Mz), 6.85 (1H, d, J=3 Mz), 7.15 (1H, d, J=3 Mz)

Mass (m/z): 305 (M$^+$), 259

(4) 2,3-Dihydro-6-ethoxycarbonyl-7-hydroxy-9-methylthio5-oxo-5H-pyrido[1,2,3-de]-1,4-benzoxazine mp 157°–160° C.

IR (Nujol): 1670, 1650, 1570 cm$^{-1}$

NMR (CDCl$_3$, δ): 1.48 (3H, t, J=7 Mz), 2.52 (3H, s), 4.1–4.4 (4H, m), 4.50 (2H, q, J=7 Mz), 7.11 (1H, d, J=2 Mz), 7.56 (1H, d, J=2 Mz), 14.2 (1H, s)

Mass (m/z): 321 (M$^+$), 275

(5) 2,3-Dihydro-6-ethoxycarbonyl-7-hydroxy-5-oxo-5Hpyrido[1,2,3-de]-1,4-benzothiazine mp: 127°–132° C.

IR (Nujol): 1660, 1640, 1620, 1560 cm$^{-1}$

NMR (CDCl$_3$, δ): 1.48 (3H, t, J=7 Mz ), 3.0-3.2 (2H, m), 4.4–4.6 (4H, m), 7.12 (1H, t, J=7 Mz ), 7.50 (1H, d, J=7 Mz), 7.96 (1H, d, J=7 Mz ), 14.2 (1H, s)

Mass (m/z): 291 (M$^+$), 245

(6) 2,3-Dihydro-6-ethoxycarbonyl-7-hydroxy-9-methoxy-5-oxo-5H-pyrido[1,2,3-de]-1,4-benzothiazine mp: 182°–185° C.

IR (Nujol): 1650, 1590, 1570 cm$^{-1}$

NMR (DMSO-d$_6$, δ): 1.29 (3H, t, J=7 Mz), 3.1–3.3 (2H, m), 380 (3H, s), 42–44 (4H, m), 7.22 (1H, d, J=2 Mz ), 7.28 (1H, d, J=2 Mz )

(7) 2,3-Dihydro-6-ethoxycarbonyl-7-hydroxy-9-methoxy-3-methyl-5-oxo-5H-pyrido[1,2,3-de]-1,4-benzoxazine mp: 158°–160° C.

IR (Nujol): 1655, 1630, 1580, 1490 cm$^{-1}$

NMR (CDCl$_3$, δ): 1.38 (3H, d, J=7 Mz), 1.49 (3H, t, J=7 Mz), 3.88 (3H, s), 4.0–4.6 (4H, m), 5.0–5.1 (1H, m), 6.88 (1H, d, J=2 Mz), 7.19 (1H, d, J=2 Mz)

Mass (m/z): 319 (M$^+$), 273

EXAMPLE 3

A mixture of 2,3-dihydro-6-ethoxycarbonyl-7-hydroxy-5-oxo-5H-pyrido[1,2,3-de]-1,4-benzoxazine (6 g) and N-methylaniline (4 ml) in pyridine (30 ml) was stirred at 125° C. for 4 hours. The solvent was evaporated, and the residue was purified by column chromatography on silica gel (200 g) eluting with a mixture of chloroform and methanol (5:1). The product was recrystallized from a mixture of ethanol and isopropyl ether to give pale brown crystals of 2,3-dihydro-7-hydroxy-6-(N-methyl-N-phenylcarbamoyl)-5-oxo-5H-pyrido[1,2,3-de]-1,4-benzoxazine (1.7 g).

mp: 200°–202° C. (dec.)

IR (Nujol): 1645, 1610, 1585, 1500 cm$^{-1}$

NMR (DMSO-d$_6$, δ): 3.30 (3H, s), 3.97 (2H, broad s), 4.25 (2H, broad s), 7.0–7.5 (8H, m), 11.4 (1H, broad s)

Mass (m/z): 336 (M$^+$), 229

EXAMPLE 4

The following compounds were obtained according to a similar manner to that of Example 3.

(1)   2,3-Dihydro-7-hydroxy-6-(1-indolinylcarbonyl)-5-oxo-5H-pyrido[1,2,3-de]-1, 4-benzoxazine mp: 260°–261° C. (dec.)

IR (Nujol): 1630, 15 95, 1570, 1485 cm$^{-1}$

NMR (DMSO-d$_6$, δ): 3.09 (2H, t, J=8.5 Mz), 3.92 (2H, t. J=8.5 Mz), 4.11 (2H, t, J=4 Mz), 4.38 (2H, t, J=4 Mz), 7.0–7.7 (6H, m), 8.19 (1H, d, J=8 Mz ), 11.5 (1H, broad s)

Mass (m/z): 348 (M$^+$)

(2)   2,3-Dihydro-7-hydroxy-6-(N-phenylcarbamoyl)-5-oxo-5H-pyrido[1,2,3-de]-1,4-benzoxazine mp: 217°–218° C.

IR (Nujol): 1660, 1620, 1590, 1570, 1490 cm$^{-1}$ NMR (DMSO-d$_6$, δ): 4.21 (2H, t, J=5 Mz), 4.44 (2H, t, J=5 Mz), 7.1–7.8 (8H, m), 12.6 (1H, s)

Mass (m/z): 322 (M$^+$)

(3) 2,3-Dihydro-9-fluoro-7-hydroxy-6-(N-methyl-N-phenylcarbamoyl)-5-oxo-5H-pyrido[1,2,3-de]-1,4-benzoxazine mp: 198°–200° C.

IR (Nujol): 1640, 1610, 1580, 1500 cm$^{-1}$

NMR (CDCl$_3$, δ): 3.51 (3H, s), 3.77 (2H, broad s), 4.20 (2H, broad s), 6.8–7.4 (7H, m)

Mass (m/z): 354 (M$^+$)

(4)   2,3-Dihydro-9-fluoro-7-hydroxy-6-(1-indolinyl-carbonyl)-5-oxo-5H-pyrido[1,2,3-de]-1,4-benzoxazine mp: 234°–23 7° C.

IR (Nujol) 1630, 1550 cm$^{-1}$

NMR (DMSO-d$_6$, δ): 3.09 (2H, t, J=8 Mz), 3.90 (2H, t, J=8 Hz), 4.11 (2H, s), 4.42 (2H, s), 7.0–7.5 (5H, m), 8.1 8 (1H, d, J=8 Mz), 11.7 (1H, broad s)

Mass (m/z): 366 (M$^+$), 247

(5)   2,3-Dihydro-9-methyl-7-hydroxy-6-(N-methyl-N-phenyl-carbamoyl)-5-oxo-5H-pyrido[1,2,3-de]-1,4-benzoxazine mp: 165°–168° C.

IR (Nujol): 1650, 1635, 1620, 1590, 1500 cm$^{-1}$

NMR (DMSO-d$_6$, δ): 2.26 (3H, s), 3.29 (3H, s), 3.93 (2H, s), 4.22 (2H, s), 6.91 (1H, s), 7.0–7.4 (6H, m), 11.2 (1H, broad s)

Mass (m/z): 350 (M$^+$), 243

Elemental Analysis Calcd. for C$_{20}$H$_{18}$N$_2$O$_4$: C 68.58, H 5.18, N 8.00 Found: C 68.24, H 5.24, N 7.86

(6)   2,3-Dihydro-7-hydroxy-9-methyl-6-(1-indolinyl-carbonyl)-5-oxo-5H-pyrido[1,2,3-de]-1,4-benzoxazine mp: >250° C.

IR (Nujol): 1630, 1580, 1500 cm$^{-1}$

NMR (CF$_3$COOH, δ): 2.60 (3H, s), 3.2–3.6 (2H, m), 4.2–4.7 (6H, m), 7.2–8.0 (6H, m)

Mass (m/z): 362 (M$^+$), 243

Elemental Analysis Calcd. for C$_{21}$H$_{18}$N$_2$O$_4$: C 69.60, H 5.00, N 7.73 Found: C 69.32, H 5.01, N 7.71

(7)   2,3-Dihydro-7-hydroxy-9-methoxy-6-(N-methyl-N-phenylcarbamoyl)-5-oxo-5H-pyrido[1,2,3-de]-1,4-benzoxazine mp: 138°–141° C.

IR (Nujol): 1630, 1590, 1500 cm$^{-1}$

NMR (DMSO-d$_6$, δ): 3.30 (3H, s), 3.73 (3H, s), 3.9–4.4 (4H, m), 6.7–7.5 (7H, m), 11.3 (1H, broad s)

Mass (m/z): 366 (M$^+$)

(8)   2,3-Dihydro-7-hydroxy-9-methoxy-6-(1-indolinyl-carbonyl)-5-oxo-5H-pyrido[1,2,3-de]-1,4-benzoxazine mp: 234°–236° C.

IR (Nujol): 1650, 1610, 1550, 1500 cm$^{-1}$

NMR (DMSO-d$_6$, δ): 3.09 (2H, t, J=8 Mz), 3.80 (3H, s), 3.90 (2H, t, J=8 Hz), 4.0–4.5 (4H, m), 6.8–7.3 (5H, m), 8.20 (1H, d, J=8 Mz)

Mass (m/z): 378 (M$^+$), 259

(9)   2,3-Dihydro-7-hydroxy-9-methylthio-6-(1-indolinyl-carbonyl)-5-oxo-5H-pyrido[1,2,3-de]-1,4-benzoxazine mp: 224°–226° C.

IR (Nujol): 1650, 1600, 1590, 1555, 1490 cm$^{-1}$

NMR (DMSO-d$_6$, δ): 2.52 (3H, s), 3.09 (2H, t, J=8 Hz), 3.90 (2H, t, J=8 Mz), 4.09 (2H, broad s), 4.38 (2H, broad s), 7.0–7.6 (5H, m), 8.18 (1H, d, J=8 Mz), 11.5 (1H, broad s)

Mass (m/z): 394 (M$^+$), 275

(10)   2,3-Dihydro-7-hydroxy-6-(1-indolinylcarbonyl)-5-oxo-5H-pyrido[1,2,3-de]-1,4-benzothiazine mp: 248°–250° C.

IR (Nujol): 1630, 1580, 1560, 1485 cm$^{-1}$

NMR (DMSO-d$_6$, δ): 3.09 (2H, t, J=8 Hz), 3.2–3.4 (2H, m), 3.90 (2H, t, J=8 Mz), 4.3–4.5 (2H, m), 7.0–7.6 (5H, m), 7.84 (1H, d, J=8 Mz), 8.18 (1H, d, J=8 Mz)

Mass (m/z): 364 (M$^+$)

(11)   2,3-Dihydro-7-hydroxy-6-(N-methyl-N-phenylcarbamoyl)-5-oxo-5H-pyrido[1,2,3-de]-1,4-benzothiazine mp: 215°–218° C.

IR (Nujol): 1640, 1605, 1580 cm$^{-1}$

NMR (CDCl$_3$, δ): 2.8–3.0 (2H, m), 3.51 (3H, s), 4.0–4 .2 (2H, m), 7.0–7.5 (7H, m), 7.90 (1H, d, J=7 Mz )

Mass (m/z) 352 (M$^+$), 245

(12)   2,3-Dihydro-7-hydroxy-6-(1-indolinylcarbonyl)-9-methoxy-5-oxo-5H-pyrido[1,2,3-de]-1,4-benzothiazine mp: 222°–225° C.

IR (Nujol): 1650, 1600, 1560 cm$^{-1}$

NMR (DMSO-d$_6$, δ): 3.08 (2H, t, J=8 Hz), 3.2–3.3 (2H, m), 3.80 (3H, s), 3.89 (2H, t, J=8 Mz), 4.3–4.5 (2H, m), 7.0–7.4 (5H, m), 8.18 (1H, d, J=8 Mz)

Mass (m/z): 394 (M$^+$)

Elemental Analysis Calcd. for C$_{21}$H$_{18}$N$_2$O$_4$S: C 63.95, H 4.60, N 7.16

Found : C 63.89, H 4.70, N 7.16 (13) 2,3-Dihydro-7-hydroxy-9-methoxy-3-methyl-6-(1-indolinylcarbonyl)-5-oxo-5H-pyrido[1,2,3-de]-1,4-benzoxazine mp: 218°–222° C.

IR (Nujol): 1630, 1585, 1560 cm$^{-1}$

NMR (DMSO-d$_6$, δ): 1.24 (3H, d, J=6 Mz), 3.09 (2H, t, J=8 Hz), 3.80 (3H, s), 3.8–4.2 (3H, m), 4.41 (1H, d, J=11 Hz), 4.8–5.0 (1H, m), 6.8–7.3 (5H, m), 8.18 (1H, d, J=8 Mz), 11.5 (1H, s)

Mass (m/z): 392 (M$^+$), 273

(14) 2,3-Dihydro-6-[(5-fluoro-1-indolinyl)carbonyl]-7-hydroxy-9-methoxy-5-oxo-5H-pyrido[1,2,3-de]-1,4-benzoxazine mp: 244°–24 8° C.

IR (Nujol): 1650, 1605, 1590, 1550, 1495 cm$^{-1}$

NMR (DMSO-d$_6$, δ): 3.10 (2H, t, J=8 Mz), 3.79 (3H, s), 3.93 (2H, t, J=8 Mz), 4.0–4.4 (4H, m), 6.8–7.2 (4H, m), 8.1–8.2 (1H, m), 11.4 (1H, s)

Mass (m/z): 396 (M$^+$), 259

Elemental Analysis Calcd. for C$_{21}$H$_{17}$NM$_2$FO$_5$: C 63.64, H 4.32, N 7.07

Found: C 63.40, H 4.13, N 6.98

EXAMPLE 5

A mixture of 2,3-dihydro-6-ethoxycarbonyl-7-hydroxy-5-oxo-5H-pyrido[1,2,3-de]-1,4-benzoxazine (0.28 g) and hydrobromic acid (47%; 0.44 ml) in acetic acid (1.5 ml) was stirred at 75° C. for 1 hour. The mixture was cooled in ice-water. The precipitates were collected, washed with water, and dried in vacuo at 60° C. to give pale brown crystals of 2,3-dihydro-6-carboxy-7-hydroxy-5-oxo-5Hpyrido[-1,2,3-de]-1,4-benzoxazine (0.19 g).

mp: 197 °–198° C. (dec.)

IR (Nujol ): 1690, 1635, 1600, 1500 cm$^{-1}$

NMR (DMSO-d$_6$, δ): 4.23 (2H, t, J=5 Mz), 4.45 (2H, t, J=5H z), 7.3–7.5 (2H, m), 7.73 (1H, dd, J=7 and 2 Mz)

Mass (m/z): 247 (M$^+$), 229

EXAMPLE 6

The following compounds were obtained according to a similar manner to that of Example 5.

(1) 2,3-Dihydro-6-carboxy-7-hydroxy-9-methylthio-5-oxo-5H-pyrido[1,2,3-de]-1,4-benzoxazine mp: 200°–230° C. (dec.)

IR (Nujol): 1680, 1630, 1600, 1500 cm$^{-1}$

NMR (DMSO-d$_6$, δ): 2.55 (3H, s), 4.1–4.3 (2H, m), 4.4–4.5 (2H, m), 7.34 (1H, d, J=2 Mz), 7.44 (1H, d, J=2 Mz)

Mass (m/z): 293 (M$^+$), 275

(2) 2,3-Dihydro-6-carboxy-7-hydroxy-9-methoxy-5-oxo-5Hpyrido[-1,2,3-de]-1,4-benzothiazine IR (Nujol): 1690, 1630, 1595 cm$^{-1}$ NMR (DMSO-d$_6$, δ): 3.2–3.4 (2H, m), 3.85 (3H, s), 4.4–4.5 (2H, m), 7.30 (1H, d, J=3 Mz), 7.42 (1H, d, J=3 Mz)

Mass (m/z): 293 (M$^+$), 275

EXAMPLE 7

Phosphorus trichloride (0.353 ml) was added dropwise to a water-cooled solution of N-methyl-4-fluoroaniline (3.04 g) in toluene (18 ml). The mixture was stirred at room temperature for 30 minutes. 6-Carboxy-2,3-dihydro-7-hydroxy-5-oxo-5H-pyrido[1,2,3-de]-1,4-benzoxazine (2 g) was added thereto, and the resulting mixture was stirred at 100° C. for 2 hours. Water (20 ml) and 4N sodium hydroxide (15 ml) were added thereto. The insoluble material was filtered and the filtrate was separated. The aqueous layer was acidified with hydrochloric acid and extracted with chloroform. The extract was dried over magnesium sulfate, filtered, and concentrated. The residue was recrystallized from a mixture of ethanol and isopropyl ether to give pale brown crystals of 2,3-dihydro-7-hydroxy-6-[N-(4-fluorophenyl)-N-methylcarbamoyl]-5-oxo-5H-pyrido[1,2,3-de]-1,4-benzoxazine (2.1 g).

mp: 179°–181° C. (dec.)

IR (Nujol): 1645, 1610, 1585, 1510 cm$^{-1}$

NMR (DMSO-d$_6$, δ): 3.28 (3H, s), 3.96 (2H, broad s), 4.26 (2H, broad s), 7.0–7.5 (7H, m), 11.3 (1H, s)

Mass (m/z): 354 (M$^+$), 229

Elemental Analysis Calcd. for C$_{19}$H$_{15}$N$_2$FO$_4$: C 64.40, H 4.27, N 7.91

Found: C 64.25, H 4.30, N 7.70

EXAMPLE 8

The following compounds were obtained according to a similar manner to that of Example 7.

2,3-Dihydro-6-[N-methyl-N-(4-methylthiophenyl)-carbamoyl]-7-hydroxy-5-oxo-5H-pyrido[1,2,3-de]-1,4-benzoxazine mp: 157°–162° C.

IR (Nujol): 1645, 1610, 1570, 1495 cm$^{-1}$

NMR (DMSO-d$_6$, δ): 2.37 (3H, s), 3.27 (3H, s), 3.98 (2H, broad s), 4.26 (2H, broad s), 7.0–7.5 (7H, m), 11.3 (1H, broad s)

Mass (m/z): 382 (M$^+$), 229

(2) 2,3-Dihydro-7-hydroxy-9-methylthio-5-oxo-6-(N-phenylcarbamoyl)-5H-pyrido[1,2,3-de]-1,4-benzoxazine mp: 239°–240° C.

IR (Nujol): 3450, 1640, 1600, 1550 cm$^{-1}$

NMR (DMSO-d$_6$, δ): 2.47 (3H, s), 3.9–4.1 (2H, m), 4.2–4.4 (2H, m), 6.9–7.7 (7H, m)

Mass (m/z): 368 (M$^+$)

(3) 2,3-Dihydro-7-hydroxy-9-methylthio-6-(N-methyl-N-phenylcarbamoyl)-5-oxo-5H-pyrido[1,2,3-de]-1,4-benzoxazine mp: 200°–208° C.

IR (Nujol): 1640, 1610, 1580, 1490 cm$^{-1}$

NMR (DMSO-d$_6$, δ): 2.46 (3H, s), 3.30 (3H, s), 3.95 (2H, s), 4.25 (2H, s), 7.0–7.4 (7H, m), 11.3 (1H, broad s)

Mass (m/z): 382 (M$^+$)

(4) 2,3-Dihydro-7-hydroxy-6-(N-methyl-N-phenylcarbamoyl)-9-methoxy-5-oxo-5H-pyrido[1,2,3-de]-1,4-benzothiazine mp: 142°–144° C.

IR (Nujol): 1645, 1620, 1590, 1570 cm$^{-1}$

NMR (DMSO-d$_6$, δ): 3.10 (2H, s), 3.29 (3H, s), 3.74 (3H, s), 4.22 (2H, s), 7.0–7.4 (7H, m)

EXAMPLE 9

The following compounds were obtained according to a similar manner to that of Example 3.

(1) 2,3-Dihydro-6-(4-fluoro-1-indolinylcarbonyl)-7-hydroxy-9-methoxy-5-oxo-5H-pyrido[1,2,3-de]-1,4-benzoxazine mp: 232°–235° C.

IR (Nujol): 1660, 1620, 1610, 1550, 1500 cm$^{-1}$

NMR (DMSO-d$_6$, δ): 3.12 (2H, t, J=8 Hz ), 3.80 (3H, s), 3.9–4.5 (6H, m), 6.8–7.4 (4H, m), 8.01 (1H, d, J=8 Hz), 11.5 (1H, s)

Mass (m/z): 396 (M$^+$)

(2) 2,3-Dihydro-6-(6-fluoro-1-indolinylcarbonyl)-7-hydroxy-9-methoxy-5-oxo-5H-pyrido[1,2,3-de]-1,4-benzoxazine mp: 232°–235° C.

IR (Nujol): 1650, 1610, 1590, 1560, 1495 cm$^{-1}$ $^{-1}$

NMR (DMSO-d$_6$, δ): 3.06 (2H, t, J=8 Mz), 3.80 (3H, s), 3.96 (2H, t, J=8 Mz), 4.0–4.5 (4H, m), 6.8–7.4 (4H, m), 7.92 (1H, dd, J=10 and 2 Mz), 11.5 (1H, s)

Mass (m/z): 396 (M$^+$)

(3) 2,3-Dihydro-6-(5-chloro-1-indolinylcarbonyl)-7-hydroxy-9-methoxy-5-oxo-5H-pyrido[1,2,3-de]-1,4-benzoxazine mp: 235°–240° C.

IR (Nujol): 1650, 1590, 1550 cm$^{-1}$

NMR (DMSO-d$_6$, δ): 3.10 (2H, t, J=8 Hz), 3.80 (3H, s), 3.93 (2H, t, J=8 Mz), 4.0–4.5 (4H, m), 6.8–7.4 (4H, m), 8.15 (1H, d, J=8 Hz)

Mass (m/z): 412 (M$^+$)

(4) 2,3-Dihydro-7-hydroxy-9-methoxy-6-(5-nitro-1-indolinylcarbonyl)-5-oxo-5H-pyrido[1,2,3-de]-1,4-benzoxazine mp 233°–234° C.

IR (Nujol): 1650, 1590, 1550, 1495 cm$^{-1}$

NMR (DMSO-d$_6$, δ): 3.21 (2H, t, J=8 Hz ), 3.80 (3H, s), 3.9–4.2 (4H, m), 4.3–4.5 (2H, m), 6.87 (1H, d, J=2 Mz), 7.14 (1H, d, J=2 Mz), 8.1–8.4 (3H, m), 11.4 (1H, s)

Mass (m/z): 423 (M$^+$)

(5) 2,3-Dihydro-7-hydroxy-9-methoxy-6-(5-methyl-1-indolinylcarbonyl)-5-oxo-5H-pyrido[1,2,3-de]-1,4-benzoxazine mp: 245°–246° C.

IR (Nujol): 1630, 1615, 1570, 1520 cm$^{-1}$

NMR (DMSO-d$_6$, δ): 2.29 (3H, s), 3.04 (2H, t, J=8 Hz), 3.80 (3H, s), 3.8–4.4 (6H, m), 6.84 (1H, d, J=2 Mz), 7.0–7.2 (3H, m), 8.05 (1H, d, J=8 Mz), 11.4 (1H, s)

Mass (m/z): 392 (M$^+$)

EXAMPLE 10

A mixture of 2,3-dihydro-7-hydroxy-9-methoxy-6-(N-methyl-N-phenylcarbamoyl)-5-oxo-5H-pyrido[1,2,3-de]-1,4-benzothiazine (1 g) and m-chloroperoxybenzoic acid (0.5 g) in dichloromethane (50 ml) was stirred at 5° C. for 1 hour. The insoluble material was filtered and the filtrate was concentrated in vacuo. The residue (1.5 g) was recrystallized from acetone to give pale yellow crystals of 2,3-dihydro-7-hydroxy-9-methoxy-6-(N-methyl-N-phenylcarbamoyl)-5-oxo-5H-pyrido[1,2,3-de]-1,4benzothiazine 1-oxide (0.86 g).

mp: 230°–232° C. (dec.)

IR (Nujol): 1640, 1620, 1590, 1565, 1490 cm$^{-1}$

NMR (DMSO-d$_6$, δ): 3.0–3.5 (2H: m), 3.31 (3H, s), 3.83 (3H, s), 3.7–4.0 (1H, m), 4.7–5.0 (1H, m), 7.1–7.8 (7H, m), 11.7 (1H, s)

Mass (m/z): 291

EXAMPLE 11

A mixture of 2,3-dihydro-7-hydroxy-9-methoxy-6-(N-methyl-N-phenylcarbamoyl)-5-oxo-5H-pyrido[1,2,3-de]-1,4benzothiazine (1 g) and m-chloroperoxybenzoic acid (1 g) in dichloromethane (50 ml) was stirred at room temperature overnight. The solvent was evaporated and the residue was purified by column chromatography on silica gel (20 g) eluting with a mixture of chloroform and ethanol (10:1). The product was washed with ethanol to give pale brown crystals of 2,3-dihydro-7-hydroxy-9-methoxy-6-(N-methyl-N-phenylcarbamoyl)-5-oxo-5H-pyrido[1,2,3-de]-1,4-benzothiazine 1,1-dioxide (0.52 g).

mp: 318°–323° C. (dec.)

IR (Nujol): 3250, 1640, 1625, 1590, 1570, 1490 cm$^{-1}$

NMR (DMSO-d$_6$, δ): 3.31 (3H, s), 3.84 (3H, s), 3.7–4.0 (2H, m), 4.3–4.7 (2H, m), 7.0–7.8 (7H, m), 11.9 (1H, broad s)

Mass (m/z): 307

EXAMPLE 12

The following compounds were obtained according to a similar manner to that of Example 1.

(1) 2,3-Dihydro-3,3-dimethyl-6-ethoxycarbonyl-7-hydroxy-9-methoxy-5-oxo-5H-pyrido[1,2,3-de]-1,4-benzoxazine mp: 150°–153° C.

NMR (CDCl$_3$, δ): 1.47 (3H, t, J=7 Mz), 1.71 (6H, s), 3.85 (3H, s), 3.92 (2H, s), 4.52 (2H, q, J=7 Mz), 6.82 (1H, d, J=3 Mz), 7.18 (1H, d, J=3 Mz)

(2) 2,3-Dihydro-6-ethoxycarbonyl-7-hydroxy-10-methoxy-5-oxo-5H-pyrido[1,2,3-de]-1,4-benzoxazine mp: 212°–215° C.

IR (Nujol): 1660, 1625, 1595, 1570, 1500 cm$^{-1}$

NMR (CDCl$_3$, δ): 1.47 (3H, t, J=7 Mz), 4.01 (3H, s), 4.15–4.5 (4H, m), 4.48 (2H, q, J=7 Mz), 6.88 (1H, d, J=9 Mz), 7.75 (1H, d, J=9 Mz), 14.3 (1H, s)

Mass (M/z): 305 (M$^+$)

EXAMPLE 13

The following compounds were obtained according to a similar manner to that of Example 3.

(1) 2,3-Dihydro-6-(5-methoxy-1-indolinylcarbonyl)-7 hydroxy-9-methoxy-5-oxo-5H-pyrido[1,2,3-de]-1,4-benzoxazine mp: 212°–214° C.

IR (Nujol): 1645, 1615, 1590, 1550, 1500 cm$^{-1}$

NMR (DMSO-d$_6$, δ): 3.06 (2H, t, J=8 Hz), 3.74 (3H, s), 3.80 (3H, s), 3.89 (2H, t, J=8 Mz), 4.0–4.2 (2H, m), 4.3–4.45 (2H, m), 6.7–7.2 (4H, m), 8.08 (1H, d, J=7 Mz), 11.4 (1H, s)

Mass (m/z): 259

(2) 2,3-Dihydro-6-(5,6-difluoro-1-indolinylcarbonyl)-7 hydroxy-9-methoxy-5-oxo-5H-pyrido[1,2,3-de]-1,4-benzoxazine mp: 247°–250° C.

IR (Nujol): 1650, 1595, 1555, 1500 cm$^{-1}$

NMR (DMSO-d$_6$, δ): 3.09 (2H, t, J=8 Hz), 3.79 (3H, s), 3.96 (2H, t, J=8 Mz), 4.0–4.2 (2H, m), 4.3–4.5 (2H, m), 6.85 (1H, d, J=3 Mz), 7.14 (1H, d, J=3 Mz), 7.3–7.5 (1H, m), 8.0–8.2 (1H, m), 11.5 (1H, s)

Mass (m/z): 414 (M$^+$)

(3) 2,3-Dihydro-6-[(3,4-dihydro-2H-1,4-benzoxazin-4-yl)-carbonyl]-7-hydroxy-9-methoxy-5-oxo-5H-pyrido[1,2,3-de]-1,4-benzoxazine mp: 182°–184° C.

IR (Nujol): 1640, 1580, 1500 cm$^{-1}$

NMR (DMSO-d$_6$, δ): 3.78 (3H, s), 3.6–4.4 (8H, m), 6.7–7.2 (6H, m), 11.5 (1H, s)

Mass (m/z): 394 (M$^+$)

(4) 2,3-Dihydro-6-[(1,2,3,4-tetrahydroisoquinolin-2-yl)carbonyl]-7-hydroxy-9-methoxy-5-oxo-5H-pyrido[-1,2,3-de]-1,4-benzoxazine mp: 198°–202° C.

IR (Nujol): 1630, 1560, 1545, 1510 cm$^{-1}$

NMR (DMSO-d$_6$, δ): 2.7–2.9 (2H, m), 3.5–3.8 (2H, m), 3.79 (3H, s), 4.0–4.15 (2H, m), 4.3–4.4 (2H, m), 4.5–4.8 (2H, m), 6.82 (1H, d, J=2 Mz), 7.0–7.4 (5H, m)

Mass (m/z): 392 (M$^+$)

(5) 2,3-Dihydro-6-[(1,2,3,4-tetrahydroquinolin-1-yl)carbonyl]-7-hydroxy-9-methoxy-5-oxo-5H-pyrido[1,2,3-de]-1,4-benzoxazine mp: 134°–138° C.

IR (Nujol): 1630, 1565, 1495 cm$^{-1}$

NMR (DMSO-d$_6$, δ): 1.8–2.1 (2H, m), 2.7–2.9 (2H, m), 3.77 (3H, s), 3.8–4.5 (6H, m), 6.8–7.3 (6H, m) 392 (M$^+$)

Mass (m/z): 392 (M$^+$)

(6) 2,3-Dihydro-6-[1,2,3,4-tetrahydro-4-methylquinoxalin-1-yl)carbonyl]-7-hydroxy-9-methoxy-5-oxo-5H-pyrido[-1,2,3-de]-1,4-benzoxazine mp: 172°–175° C.

IR (Nujol): 1645, 1630, 1570, 1500 cm$^{-1}$

NMR (DMSO-d$_6$, δ): 2.91 (3H, s), 3.77 (3H, s), 3.9–4.4 (8H, m), 6.6–7.2 (6H, m)

Mass (m/z): 407 (M$^+$)

(7) 2,3-Dihydro-6-(2-methyl-1-indolinylcarbonyl)-7-hydroxy-9-methoxy-5-oxo-5H-pyrido[1,2,3-de]-1,4-benzoxazine mp: 239°–241° C.

IR (Nujol): 1650, 1625, 1585, 1500, 1490 cm$^{-1}$

NMR (DMSO-d$_6$, δ): 1.07 (3H, d, J=6 Mz), 3.2–3.5 (2H, 10 m), 3.80 (3H, s), 4.0, 4.2 (2H, m), 4.2–4.5 (3H, m), 6.8–7.4 (5H, m), 8.16 (1H, d, J=7 Mz), 11.5 (1H, s)

Mass (m/z): 392 (M$^+$)

(8) 2,3-Dihydro-7-hydroxy-10-methoxy-6-(1-indolinylcarbonyl)-5-oxo-5H-pyrido[1,2,3-de]-1,4-benzoxazine mp: 248°–250° C.

IR (Nujol): 1625, 1590, 1560 cm$^{-1}$

NMR (DMSO-d$_6$, δ): 3.08 (2H, t, J=8 Mz), 3.89 (3H, s), 3.8–4.2 (4H, m), 4.3–4.4 (2H, m), 7.0–7.3 (4H, m), 7.62 (1H, d, J=9 Mz), 8.17 (1H, d, J=8 Mz)

Mass (m/z): 378 (M$^+$)

(9) 2,3-Dihydro-3,3-dimethyl-7-hydroxy-9-methoxy-6-(1-indolinylcarbonyl)-5-oxo-5H-pyrido[1,2,3-de]-1,4-benzoxazine mp: 198°–200° C.

IR (Nujol): 1630, 1580, 1490 cm$^{-1}$

NMR (DMSO-d$_6$, δ): 1.60 (6H, s), 3.09 (2H, t, J=8HZ), 3.79 (3H, s), 3.88 (2H, t, J=8 Mz), 4.04 (2H, s), 6.8–7.4 (5H, m), 8.16 (1H, d, J=8 Mz) 406 (M$^+$)

Mass (m/z):

(10) 2,3-Dihydro-7-hydroxy-9-nitro-6-(1-indolinylcarbonyl)-5-oxo-5H-pyrido[1,2,3-de]-1,4-benzoxazine mp: 246°–248° C.

IR (Nujol): 1650, 1630, 1605, 1570, 1530, 1500 cm$^{-1}$

NMR (DMSO-d$_6$, δ): 3.10 (2H, t, J=8 Hz), 3.92 (2H, t, J=8 Mz), 4.0–4.3 (2H, m), 4.4–4.6 (2H, m), 6.9–7.4 (3H, m), 7.90 (1H, d, J=2 Mz), 8.18 (1H, d, J=8 Hz), 8.50 (1H, d, J=2 Mz)

Mass (m/z): 393 (M$^+$)

Elemental Analysis Calcd. for C$_{20}$H$_{15}$N$_3$O$_6$: C 61.07, H 3.84, N 10.68

Found : C 60.94, H 3.66, N 10.51

EXAMPLE 53

The following compound was obtained according to a similar manner to that of Example 5.

6-Carboxy-2,3-dihydro-7-hydroxy-9-methoxy-5-oxo-5H-pyrido[1,2,3-de]-1,4-benzoxazine mp: 192°–195° C.

IR (Nujol): 1690, 1630, 1600, 1490 cm$^{-1}$

EXAMPLE 15

The following compound was obtained according to similar manner to that of Example 7.

2,3-Dihydro-6-[(3,4-dihydro-2H-1,4-benzothiazin-4-yl)carbonyl]-7-hydroxy-9-methoxy-5-oxo-5H-pyrido-1,2,3-de]-1,4-benzoxazine mp: 185–188° C.

IR (Nujol): 1620, 1610, 1590, 1505 cm$^{-1}$

NMR (DMSO-d$_6$, δ): 3.2–3.5 (4H, m), 3.76 (3H, s), 3.9–4.1 (2H, m), 4.2–4.4 (2H, m), 6.7–7.2 (6H, m)

Mass (m/z): 410 (M$^+$)

EXAMPLE 16

The following compound was obtained according to a similar manner to that of Example 10.

2,3-Dihydro-7-hydroxy-6-(N-methyl-N-phenylcarbamoyl)-5-oxo-5H-pyrido[1,2,3-de]-1,4-benzothiazine-1-oxide mp: 234°–239° C. (dec.)

IR (Nujol): 1645, 1625, 1590, 1495 cm$^{-1}$

NMR (DMSO-d$_6$, δ): 2.9–3.4 (2H, m), 3.31 (3H, s), 3.7–4.0 (1H, m), 4.8–5.0 (1H, m), 7.0–7.5 (6H, m), 7.9–8.2 (2H, m), 11.8 (1H, s)

Mass (m/z): 369 (M+1)

EXAMPLE 17

A mixture of 6-carboxy-2,3-dihydro-7-hydroxy-9-methoxy-5-oxo-5H-pyrido[1,2,3-de]-1,4-benzoxazine (1.5 g), 2-ethoxycarbonylindoline (2.3 g) and 1,3-dicyclohexylcarbodiimide (3 g) in toluene (20 ml) was stirred at 90° C. for 3 hours. The mixture was filtered and the filtrate was concentrated in vacuo. The residue was purified by column chromatography on silica gel eluting with chloroform-methanol (30:1) to give 2,3-dihydro-6-(2-ethoxycarbonyl-1-indolinylcarbonyl)-7-hydroxy-9-methoxy-5-oxo-5H-pyrido[1,2,3-de]-1,4-benzoxazine (2.8 g).

mp: 135°–138° C.

NMR (DMSO-d$_6$, δ): 0.79 (3H, t, J=7 Mz), 2.9–4.3 (8H, m), 3.73 (3H, s), 5.2–5.4 (1H, m), 6.6–7.3 (5H, m), 8.26 (1H, d, J=8 Mz)

Mass (m/z): 450 (M$^+$)

EXAMPLE 18

A mixture of 2,3-dihydro-6-(2-ethoxycarbonyl-1-indolinylcarbonyl)-7-hydroxy-9-methoxy-5-oxo-5Hpyrido[1,2,3-de]-1,4-benzoxazine (2.8 g), 1N-sodium 35 hydroxide (20 ml), ethanol (20 ml) and tetrahydrofuran (20 ml was stirred for 2 hours at room temperature. The solvent was evaporated. The residue was dissolved in water and washed with ethyl acetate. The aqueous layer was acidified with hydrochloric acid to give precipitates, which were collected and washed with ethanol to afford crystals of 2,3-dihydro-6-(2-carboxy-1-indolinylcarbonyl)-7- hydroxy-9-methoxy-5-oxo-5H-pyrido[1,2,3-de]-1,4 -benzoxazine (1.6 g).

mp: 185°–190° C.

IR (Nujol): 1710, 1660, 1610, 1560, 1500 cm$^{-1}$

NMR (DMSO-d$_6$, δ): 3.0–3.3 (2H, m), 3.79 (3H, S) 4.0–4.2 (2H, m), 4.3–4.5 (2H, m), 4.8–5.0 (1H, m), 6.8–7.3 (5H, m), 8.20 (1H, d, J=8 Hz)

Mass (m/z): 404

EXAMPLE 19

A mixture of 2,3-dihydro-7-hydroxy-9-methoxy-6-(1-indolinylcarbonyl)-5-oxo-5H-pyrido[1,2,3-de]-1,4-benzoxazine (3 g) and phosphorus oxychloride (2.2 ml) was stirred at 80° C. for 1 hour. The mixture was poured into ice-water and the precipitates were collected and washed with water to give yellow crystals of 2,3-dihydro-7-chloro-9-methoxy-6-(1-indolinylcarbonyl)-5-oxo-5H-pyrido[1,2,3-de]-1,4-benzoxazine (2.8 g).

mp: 158°–160° C.

NMR (DMSO-d$_6$, δ): 3.15 (2H, t, J=8 Mz), 3.85 (3H, s), 3.7–4.5 (6H, m), 6.9–7.4 (5H, m), 8.15 (1H, d, J=7 Mz )

Mass (m/z): 396 (M$^+$)

EXAMPLE 20

A mixture of 2,3-dihydro-7-chloro-9-methoxy-6-(1-indolinylcarbonyl)-5-oxo-5H-pyrido[1,2,3-de]-1,4-benzoxazine (1 g), ammonia in ethanol (13 ml) and chloroform (20 ml) was heated at 100° C. in a sealed tube for 4 days. The solvent was evaporated and the residue was purified by column chromatography on silica gel eluting with chloroform-methanol (20:1) to give crystals of 2,3-dihydro-7-amino-9-methoxy-6-(1-indolinyl-carbonyl)-5-oxo-5H-pyrido[1,2,3-de]-1,4-benzoxazine (0.35 mp: 130°–140° C.

IR (Nujol): 3350, 3200, 1620, 1580, 1500 cm$^{-1}$

NMR (DMSO-d$_6$, δ): 3.06 (2H, t, J=8 Mz), 3.80 (3H, s), 3.7–4.4 (6H, m), 6.7–7.4 (7H, m), 8.1–8.3 (1H, m)

Mass (m/z): 377 (M$^+$)

EXAMPLE 21

To a solution of diethyl malonate (0.54 g) in N,N-dimethylacetamide (10 ml) was added sodium hydride (60%; 135 mg), and the mixture was stirred at room temperature for 30 minutes. To the mixture was added 3,4-dihydro-7-nitro-2H-1,4-benzoxazine-4,5-dicarboxylic anhydride (0.73 g), and the mixture was stirred at 120° C. for 2 hours. The mixture was poured into diluted HCl, and the precipitates were collected and washed with water to afford yellow crystals of 2,3-dihydro-6-ethoxycarbonyl-7-hydroxy-9-nitro-5-oxo-5H-pyrido[1,2,3-de]-1,4-benzoxazine (0.85 g).

mp: 198°–202° C.

NMR (DMSO-d$_6$, δ): 1.29 (3H, t, J=7 Mz), 4.0–4.2 (2H, m), 4.32 (2H, q, J=7 Mz), 4.4–4.6 (2H, m), 7.93 (1H, s), 8.44 (1H, s)

Mass (m/z): 320 (M$^+$)

EXAMPLE 22

A mixture of 2,3-dihydro-7-hydroxy-9-nitro-6-(1-indolinylcarbonyl)-5-oxo-5H-pyrido [1,2,3-de]-1,4-benzoxazine (2.5 g) and platinum oxide (0.1 g) in tetrahydrofuran (150 ml) was stirred under hydrogen (3 atm.) for 2 hours. The catalyst was removed by filtration and the filtrate was concentrated in vacuo. The residue was purified by column chromatography on silica gel (60 g) eluting with chloroform-methanol (20:1). The desired product was washed with ethanol to give crystals of 2,3-dihydro-9-amino-7-hydroxy-6-(1-indolinylcarbonyl)-5-oxo-5H-pyrido[1,2,3-de]-1,4-benzoxazine (1.2 g).

mp: 195°–202° C.

IR (Nujol): 3400, 3250, 1620, 1610, 1590, 1505 cm$^{-1}$

NMR (DMSO-d$_6$, δ): 3.08 (2H, t, J=8 Mz), 3.90 (2Hr t, J=8 Hz), 3.9–4.1 (2H, m), 4.2–4.4 (2H, m), 6.51 (1H, d, J=2 Mz), 6.77 (1H, d, J=2 Mz), 7.0–7.4 (3H, m), 8.17 (1H, d, J=8 Mz)

Mass (m/z): 244

EXAMPLE 23

A mixture of 2,3-dihydro-7-hydroxy-9-nitro-6-(1-indolinylcarbonyl)-5-oxo-5H-pyrido[1,2,3-de]-1,4-benzoxazine (2.7 g) and acetic anhydride (0.79 g) in pyridine (4 ml) was stirred at room temperature for 1 hour. The mixture was concentrated in vacuo. The residue containing 2,3-dihydro-7-acetoxy-9-nitro-6-(1-indolinylcarbonyl)-5-oxo-SH-pyrido [1,2,3-de]-1,4-5 -benzoxazine was reduced catalytically in a similar manner to that of Example 22 to give crystals of 2,3-dihydro-7-acetoxy-9-amino-6-(1-indolinylcarbonyl)-5-oxo-5H Hpyrido[1,2,3-de]-1,4-benzoxazine (1.7 g).

mp: 220°–225° C.

IR (Nujol): 3400, 3250, 1780, 1640, 1630, 1590, 1500 cm$^{-1}$

NMR (DMSO-d$_6$, δ): 2.31 (3H, s), 3.08 (2H, t, J=8 Mz), 3.8–4.5 (6H, m), 6.42 (1H, d, J=2 Mz), 6.61 (1H, d, J=2 Mz), 7.0–7.4 (3H, m), 8.10 (1H, d, J=8 Hz)

EXAMPLE 24

A mixture of 2,3-dihydro-7-acetoxy-9-amino-6-(1-indolinylcarbonyl)-5-oxo-5H-pyrido[1,2,3-de]-1,4-benzoxazine (1.5 g) and potassium carbonate (0.5 g) in N,N-dimethylformamide (10 ml) was stirred at room temperature for 1 hour. The mixture was poured into cold diluted hydrochloric acid and extracted with ethyl acetate. The extract was washed with water and evaporated. The residue (1 g) was purified by column 10 chromatography on silica gel eluting with chloroform-methanol (30:1) to give crystals of 2,3-dihydro-9-acetylamino-7-hydroxy-6-(1-indolinyl-carbonyl)-5-oxo-5H-pyrido[1,2,3-de]-1,4-benzoxazine (0.72 g).

mp: 223°–225° C.

IR (Nujol): 3350, 1675, 1630, 1610, 1565 cm$^{-1}$

NMR (DMSO-d$_6$, δ) 2.04 (3H, s), 3.11 (2H, t, J=8 Hz), 3.94 (2H, t, J=8 Hz), 4.0–4.2 (2H, m), 4.3–4.5 (2H, m), 7.0–7.5 (4H, m), 7.83 (1H, s), 8.18 (1H, d, J=8 Mz), 10.0 (1H, s)

Mass (m/z): 360

EXAMPLE 25

A mixture of 6-[N-methyl-N-(4-methylthiophenyl)carbamoyl]-2,3-dihydro-7-hydroxy-5-oxo-5H-pyrido-[1,2,3-de]-1,4-benzoxazine (1 g) and m-chloroperbenzoic acid (0.5 g) in dichloromethane (50 ml) was stirred at 5° C. for 1 hour. The insoluble material was filtered and the filtrate was concentrated in vacuo. The residue was recrystallized from acetone to give pale brown crystals of 6-[N-methyl-N-(4-methylsulfinylphenyl)carbamoyl]-2,3-dihydro-7-hydroxy-5-oxo-5H-pyrido[1,2,3-de]-1,4-benzoxazine (0.82 g).

mp: 182°–184° C. (dec.)

IR (Nujol): 1640, 1620, 1585, 1490 cm$^{-1}$

NMR (DMSO-d$_6$, δ): 2.66 (3H, s), 3.34 (3H, s), 3.9–4.1 (2H, m), 4.2–4.4 (2H, m), 7.0–7.2 (2H, m), 7.4–7.7 (5H, m), 11.4 (1H, s)

Mass (m/z): 399 (M+1)

EXAMPLE 26

A mixture of 6-[N-methyl-N-(4-methylthiophenyl)carbamoyl]-2,3-dihydro-7-hydroxy-5-oxo-5H-pyrido[1,2,3-de]-1,4-benzoxazine (1 g) and m-chloroperbenzoic acid (1 g) in dichloromethane (50 ml) was stirred at room temperature for 4 hours. The solvent was evaporated and the residue was purified by column chromatography on silica gel (20 g) eluting with chloroform-methanol (10:1). The product was recrystallized from ethanol to give pale brown crystals of 6-[N-methyl-N-(4-methylsulfonylphenyl)carbamoyl]-2,3-dihydro-7-hydroxy-5-oxo-5H-pyrido[1,2,3-de]-1,4-benzoxazine (0.57 g).

mp: 181°–187° C. (dec.)

IR (Nujol): 1650, 1625, 1585, 1565, 1490 cm$^{-1}$

NMR (DMSO-d$_6$, δ): 3.17 (3H, s), 3.36 (3H, s), 3.9–4.1 (2H, m), 4.2–4.4 (2H, m), 7.0–7.2 (2H, m), 7.4–7.7 (3H, m), 7.85 (2H, d, J=8.5 Mz)

Mass (m/z): 415 (M+1)

We claim:

1. A compound of the formula

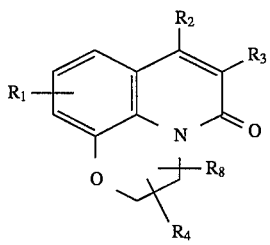

wherein:

R$^1$ is hydrogen, lower alkyl, lower alkoxy, lower alkylthio, halogen, nitro, amino or acylamino, wherein an acyl group of said acylamino is selected from the group consisting of carbamoyl, lower alkanoyl, higher alkanoyl, lower alkoxycarbonyl, higher alkoxycarbonyl, lower alkylsulfonyl, higher alkylsulfonyl, lower alkoxysulfonyl, ar(lower)alkenoyl, ar(lower)alkoxycarbonyl, aryloxycarbonyl, aryloxy(lower)alkanoyl, arylglyoxyloyl, arenesulfonyl, heterocycliccarbonyl, heterocyclic(lower)alkanoyl, heterocyclic(lower)alkenoyl and heterocyclicglyoxyloyl wherein a heterocyclic group of said heterocycliccarbonyl, heterocyclic(lower)alkanoyl, heterocyclic(lower)alkenoyl and heterocyclicglyoxyloyl is selected from the group consisting of pyrrolyl, pyrrolinyl, imidazolyl, pyrazolyl, pyridyl, dihydropyridyl, pyrimidyl, pyrazinyl, pyridazinyl, triazolyl, tetrazolyl, pyrrolidinyl, imidazolidinyl, piperidyl, piperazinyl, indolyl, isoinodolyl, indolinyl, indolizinyl, benzimidazolyl, quinolyl, tetrahydroquinolyl, isoquinolyl, tetrahydroisoquinolyl, indazolyl, quinosalinyl, tetrahydroquinoxalinyl, benzotriazolyl, oxazolyl, isoxazolyl, oxadizaolyl, morpholinyl, syndonyl, benzoxazolyl, benzoxadiazolyl, benzoxazinyl, dihydrobenzoxazinyl, thiazolyl, isothiazolyl, thiadiazolyl, dihydrothiazinyl, thiazolidinyl, thienyl, dihydrodithiinyl, dihydrodithionyl, benzothiazolyl, benzothiadiazolyl, benzothiazinyl, dihydrobenzothiazinyl, furyl, dihydrooxathiinyl, benzothienyl, benzodithiinyl and benzoxathiinyl;

R$^2$ is hydroxyl, acyloxy, halogen, amino or acylamino, wherein an acyl group of said acylamino and said acyloxy are selected from the group consisting of carbamoyl, lower alkanoyl, higher alkanoyl, lower alkoxycarbonyl, higher alkoxycarbonyl, lower alkylsulfonyl, higher alkylsulfonyl, lower alkoxysulfonyl, higher alkoxysulfonyl, aroyl ar(lower)alkanoyl, ar(lower)alkenoyl, ar(lower)alkoxycarbonyl, aryloxycarbonyl, aryloxy(lower)alkanoyl, arylglyoxyloyl, arenesulfonyl, heterocycliccarbonyl, heterocyclic(lower)alkanoyl, heterocyclic(lower)alkenoyl, heterocyclicglyoxyloyl, wherein a heterocyclic group of said heterocycliccarbonyl, heterocyclic(lower)alkanoyl, heterocyclic(lower)alkenoyl and heterocyclicglyoxylpyl is selected from the group consisting of pyrrolyl, pyrrolinyl, imidazolyl, pyrazolyl, pyridyl, dihydropyridyl, pyrimidyl, pyrazinyl, pyridazinyl, triazolyl, betrazolyl, pyrrolidinyl, imidazolidinyl, piperidyl, piperazinyl, indolyl, isoindolyl, indolinyl, indolizinyl, benzimidazolyl, quinolyl, tetrahydroquinolyl, isoquinolyl, tetrahydroisoquinolyl, indazolyl, quinoxalinyl, tetrahydroquinoxalinyl, benzotriazolyl, oxazolyl, isoxazolyl, oxadiazolyl, morpholinyl, syndonyl, benzoxazolyl, benzoxadiazolyl, benzoxazinyl, dihydrobenzoxazinyl, thiazolyl, isothiazolyl, thiadiazolyl, dihydrothiazinyl, thiazolidinyl, thienyl, dihydrodithiinyl, dihydrodithionyl, benzoxadiazolyl, benzothiadiazolyl, benzothiazinyl, dihydrobenzothiazinyl, furyl, dihydrooxathiinyl, benzothienyl, benzodithiinyl and benzoxathiinyl;

R$^3$ is hydrogen, lower alkyl, lower alkenyl, lower alkynyl, aryl, ar(lower) alkyl, carboxyl, aliphatic acyl selected from the group consisting of carbamoyl, lower alkanoyl, higher alkanoyl, lower alkoxycarbonyl, higher alkoxycarbonyl, lower alkylsulfonyl, higher alkylsulfonyl, lower alkoxysulfonyl and higher alkoxysulfonyl, aromatic acyl selected from the group consisting of aroyl, ar(lower)alkanoyl, ar(lower)alkenoyl, ar(lower)alkoxycarbonyl, aryloxycarbonyl, aryloxy(lower) alkanoyl, arylglyoxyloyl and arenesulfonyl, heterocyclic acyl which may be substituted with one to ten substituent(s) selected from the group consisting of halogen, nitro, lower alkyl, lower alkoxy, carboxy and esterified carboxy, wherein, said heterocyclic acyl is selected from the group consisting of heterocycliccarbonyl, heterocyclic,(lower) alkanoyl, heterocyclicllower)alkenoyl and heterocyclicglyoxyloyl wherein a heterocyclic group of said heterocycliccarbonyl, heterocyclic(lower)alkanoyl, heterocyclic(lower)alkenoyl and heterocyclicglyoxyloyl is selected from the group consisting of pyrrolyl, pyrrolinyl, imidazolyl, pyrazolyl, pyridyl, dihydrop, yridyl, pyrimidyl, pyrazinyl, pyridazinyl, triazolyl, tetrtazolyl, pyrrolidinyl, imidazolidinyl, piperidyl, piperazinyl, indolyl, isoindolyl, indolinyl, indolizinyl, benzimidazolyl, quinolyl, tetrahydroquinolyl, isoquinolyl, tetrahydroisoquinolyl, indazolyl, quinoxalinyl, tetrahydroquinoxalinyl, benzotriazolyl, oxazolyl, isoxazolyl, oxadizaolyl, morpholinyl, syndonyl, benzoxazolyl, benzoxadiazolyl, benzoxazinyl, dihydrobenzoxazinyl, thiazolyl, isothiazolyl, thiadiazolyl, dihydrothiazinyl, thiazolidinyl, thienyl, dihydrodithiinyl, dihydrodithionyl, benzothiazolyl, benzothiadiazolyl, benzothiazinyl, dihydrobenzothiazinyl, furyl, dihydrooxathiinyl, benzothienyl, benzodithiinyl and benzoxathiinyl, carbamoyl or substituted carbamoyl substituted with one or two substituents selected from the group consisting of lower alkyl, aryl, haloaryl, lower alkythioaryl, lower alkylsulfinylaryl and acylaryl wherein an acylgroup of said acylaryl is selected from the group consisting of carbamoyl, lower alkanoyl, higher alkanoyl, lower alkoxycarbonyl, higher alkoxycarbonyl, lower alkylsulfonyl, higher alkylsulfonyl, lower alkoxysulfonyl, higher alkoxysulfonyl, aroyl, ar(lower)alkanoyl, ar(lower)alkenoyl, ar(lower)alkoxycarboyl, aryloxycarbonyl, aryloxy (lower) alkanoyl, arylglyoxyloyl, arenesulfonyl, heterocycliccarbonyl, heterocyclic(lower)alkanoyl, heterocyclic(lower) alkenoyl and heterocyclicglyoxyloyl wherein a heterocyclic group of said heterocycliccarbonyl, heterocyclic(lower)alkanoyl, heterocyclic(lower)alkenoyl and heterocyclicglyoxyloyl is selected from the group consisting of pyrrolyl, pyrrolinyl, imidazolyl, pyrazolyl, pyridyl, dihydropyridyl, pyrimidyl, pyrazinyl, pyridazinyl, priazolyl, tetrazolyl, pyrrolidinyl, imidazolidinyl, piperidyl piperazinyl, indolyl, isoindolyl, indolinyl, indolizinyl, benzimidazolyl, quinolyl, tetrahydroquinolyl, isoquinolyl, tetrahydroisoquinolyl, indazolyl, quinoxalinyl, tetrahydroquinoxalinyl, benzotriazolyl, oxazolyl, isoazolyl, oxadiazolyl, morpholinyl, syndonyl, benzoxazolyl, benzoxadiazolyl, benzoxazinyl, dihydrobenzoxazinyl, thiazolyl, isothiazolyl, thiadiazolyl, dihydrothiazinyl, thiazolidinyl, thienyl, dihydrodithiinyl, dihydrodithionyl, benzothiazolyl, benzothiadiazolyl, benzothiazinyl, dihydrobenzothiazinyl, furyl, dihydrooxathiinyl, benzothienyl, benzodithiinyl and benzoxathiinyl;

$R^4$ is hydrogen or lower alkyl; and $R^8$ is hydrogen or lower alkyl, and a pharmaceutically acceptable salt thereof.

2. A method for the therapeutic treatment of Systemic Lupus Erythematosus which comprises administering an effective amount of a compound of claim 1 or a pharmaceutically acceptable salt thereof to human or animals.

3. A method for the therapeutic treatment of melanoma which comprises administering an effective amount of a compound of claim 1 or a pharmaceutically acceptable salt thereof to human or animals.

4. A compound of claim 1, wherein $R^3$ is carboxy; lower alkoxycarbonyl; indolinylcarbonyl, tetrahydroquinolylcarbonyl, tetrahydroisoquinolylcarbonyl, tetrahydroquinoxalinylcarbonyl, dihydrobenzoxazinylcarbonyl or dihydrobenzothiazinylcarbonyl, each of which may have one or two substituent(s) selected from the group consisting of halogen, nitro, lower alkyl, lower alkoxy, carboxy and esterified carboxy; or carbamoyl which may have one or two substituent(s) selected from the group consisting of lower alkyl, aryl, haloaryl, lower alkylthioaryl, lower alkylsulfinylaryl and acylaryl.

5. A compound of claim 4, wherein $R^3$ is carboxy; lower alkoxycarbonyl; indolinylcarbonyl, tetrahydroquinolylcarbonyl, tetrahydroisoquinolylcarbonyl, tetrahydroquinoxalinylcarbonyl, dihydrobenzoxazinylcarbonyl or dihydrobenzothiazinylcarbonyl, each of which may have one or two substituent(s) selected from the group consisting of halogen, nitro, lower alkyl, lower alkoxy, carboxy and esterified carboxy; or carbamoyl which may have one or two substituent(s) selected from the group consisting of lower alkyl, phenyl, halophenyl, lower alkylthiophenyl, lower alkylsulfinylphenyl and lower alkylsulfonylphenyl.

6. A compound of claim 5, wherein $R^1$ is hydrogen or lower alkoxy, $R^2$ is hydroxy, $R^3$ is indolinylcarbonyl which may have halogen or lower alkyl, or carbamoyl which may have one or two substituent(s) selected from the group consisting of lower alkyl, phenyl, halophenyl, lower alkylsulfinylphenyl and lower alkylsulfonylphenyl, $R^4$ is hydrogen, and $R^8$ is hydrogen.

7. A compound of claim 6, which is selected from the group consisting of 2,3-Dihydro-6-(4-fluoro-1-indolinylcarbonyl)-7-hydroxy-9-methoxy-5-oxo-5H-pyrido[1,2,3-de]-1,4-benzoxazine, 2,3-Dihydro-7-hydroxy-9-methoxy-6-(5-methyl-1-indolinylcarbonyl)-5-oxo-5H-pyrido[1,2,3-de]-1,4-benzoxazine, 2,3-Dihydro-7-hydroxy-6-[N-(4-fluorophenyl)-N-methylcarbamoyl]-5-oxo-5H-pyrido[1,2,3-de]-1,4-benzoxazine, 6-[N-Methyl-N-(4-methylsulfinylphenyl)carbamoyl]-2,3-dihydro-7-hydroxy-5-oxo-5H-Pyrido[1,2,3-de]-1,4-benzoxazine, and 6-[N-Methyl-N-(4-methylsulfonylphenyl)carbamoyl]-2,3-dihydro-7-hydroxy-5-oxo-5H-Pyrido[1,2,3-de]-1,4-benzoxazine.

8. A pharmaceutical composition which comprises, as an active ingredient, an effective amount of a compound of claim 1 or a pharmaceutically acceptable salt thereof in admixture with pharmaceutically acceptable carriers.

9. A compound of the formula

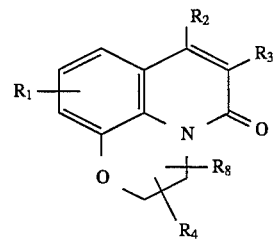

wherein $R^1$ is hydrogen or lower alkoxy;

$R^2$ is hydroxyl;

$R^3$ is indolinylcarbonyl which may have halogen or lower alkyl, or carbamoyl which may have one or two substituent(s) selected from the group consisting of lower alkyl, phenyl, halophenyl, lower alkylsulfinylphenyl and lower alkylsulfonylphenyl;

$R^4$ is hydrogen; and $R^8$ is hydrogen.

* * * * *

UNITED STATES PATENT AND TRADEMARK OFFICE
CERTIFICATE OF CORRECTION

PATENT NO. : 5,583,135

DATED : December 10, 1996

INVENTOR(S) : Matsuo et al.

It is certified that error appears in the above-identified patent and that said Letters Patent is hereby corrected as shown below:

Claim 1, at Column 31, line 54,

"alkoxysulfonyl, ar(lower)alkenoyl,"

should read --alkoxysulfonyl, higher alkoxysulfonyl, aroyl, ar(lower)alkanoyl, ar(lower)alkenoyl,--.

Column 32, line 1, "quinosalinyl"

should read --quinoxalinyl--.

Column 32, line 2, "oxadizaolyl"

should read --oxadiazolyl--.

Column 32, line 23, "heterocyclicglyoxylpyl"

should read --heterocyclicglyoxyloyl--.

Column 32, line 54, "heterocyclic,(lower)"

should read --heterocyclic (lower)--.

Column 32, lines 55 and 56, "heterocyclicllow-er)alkenoyl"

should read --heterocyclic(lower)alkenoyl--.

Column 32, line 60, "dihydrop, yridyl,"

should read --dihydropyridyl--.

UNITED STATES PATENT AND TRADEMARK OFFICE
CERTIFICATE OF CORRECTION

PATENT NO. : 5,583,135

DATED : December 10, 1996

INVENTOR(S) : Matsuo et al.

It is certified that error appears in the above-identified patent and that said Letters Patent is hereby corrected as shown below:

Column 32, line 66, "oxadizaolyl"

should read --oxadiazolyl--.

Column 33, line 10, "acylgroup"

should read --acyl group--.

Column 33, line 16, "ar(lower)alkoxycarboyl"

should read --ar(lower)alkoxycarbonyl--.

Column 33, line 23, "priazolyl,"

should read --triazolyl--.

Signed and Sealed this

Seventeenth Day of June, 1997

BRUCE LEHMAN

Attest:

Attesting Officer

Commissioner of Patents and Trademarks